(12) United States Patent
Ceri et al.

(10) Patent No.: US 8,377,455 B2
(45) Date of Patent: Feb. 19, 2013

(54) **BIOSURFACTANT COMPOSITION PRODUCED BY A NEW *BACILLUS LICHENIFORMS* STRAIN, USES AND PRODUCTS THEREOF**

(75) Inventors: Howard Ceri, Calgary (CA); Raymond J Turner, Calgary (CA); Maria Giovanna Martinotti, Sanremo (IT); Fabrizio Rivardo, Mottalciata (IT); Gianna Allegrone, Moncalieri (IT)

(73) Assignees: PAN-ECO S.A., Luxembourg (LU); University Technologies International LP, Calgary, Alberta (CA)

( * ) Notice: Subject to any disclaimer, the term of this patent is extended or adjusted under 35 U.S.C. 154(b) by 0 days.

(21) Appl. No.: 13/131,420

(22) PCT Filed: Nov. 25, 2009

(86) PCT No.: PCT/IB2009/055334
§ 371 (c)(1),
(2), (4) Date: Jul. 20, 2011

(87) PCT Pub. No.: WO2010/067245
PCT Pub. Date: Jun. 17, 2010

(65) Prior Publication Data
US 2011/0274730 A1 Nov. 10, 2011

(30) Foreign Application Priority Data
Dec. 10, 2008 (WO) ................ PCT/IB2008/003583

(51) Int. Cl.
*A61K 9/00* (2006.01)
*A61K 38/12* (2006.01)
*C12N 1/20* (2006.01)

(52) U.S. Cl. ........................ 424/400; 435/252.5; 514/2.9
(58) Field of Classification Search ........................ None
See application file for complete search history.

(56) References Cited

FOREIGN PATENT DOCUMENTS
WO WO 2004/002510 1/2004

OTHER PUBLICATIONS

International Search Report for PCT/IB2009/055334, dated Mar. 30, 2010.
Written Opinion for PCT/IB2009/055334, dated Mar. 30, 2010.
Duitman et al., "The mycosubtilin synthetase of *Bacillus subtilis* ATCC6633: A multifunctional hybrid between a peptide synthetase, an amino transferase, and a fatty acid synthase", *PNAS*, Nov. 1999, vol. 96, No. 23, pp. 13294-13299.
Di Toro et al., Intensification of the aerobic biore mediation of an actual site soil historically contaminated by polychlorinated biphenyls (PCBs) through bioaugmentation with a non acclimated, complex source of microorganisms, Mar. 2006, vol. 5, No. 11, 10 pages.
Huang et al., "Optimization of Sterilization of *Escherichia coli* in Milk by Surfactin and Fengycin Using a Response Surface Method", *Microbiol.*, 2008, vol. 56, pp. 376-381.
Seydlova et al., "Development of Membrane Lipids in the Surfactin Producer *Bacillus subtilis*", *Dept. of Genetics and Microbiology*, 2008, vol. 53, No. 4, pp. 303-307.

*Primary Examiner* — Padma Baskar
(74) *Attorney, Agent, or Firm* — Nixon & Vanderhye P.C.

(57) ABSTRACT

New *Bacillus licheniformis* strain named V9T14 that produces a new biosurfactant composition that is effective against colonization and/or bio film formation from bacteria. The new biosurfactant composition can be used in combination with biocides for preventing formation and/or for eradicating bacteria grown planktonically and/or as a biofilm, preferably on biotic and/or abiotic surfaces.

26 Claims, 26 Drawing Sheets

Growth control        V9T14

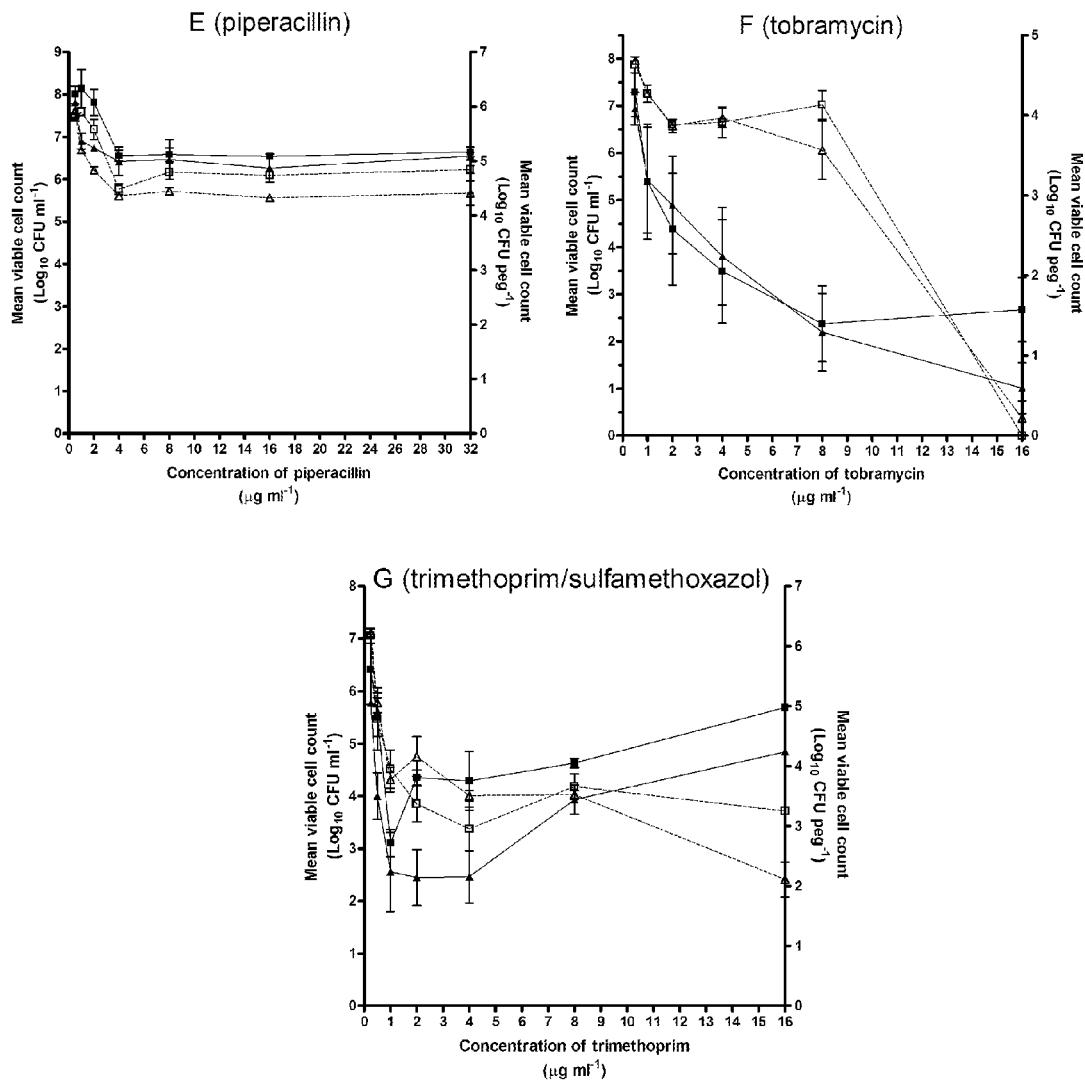
Figure 22/cont.

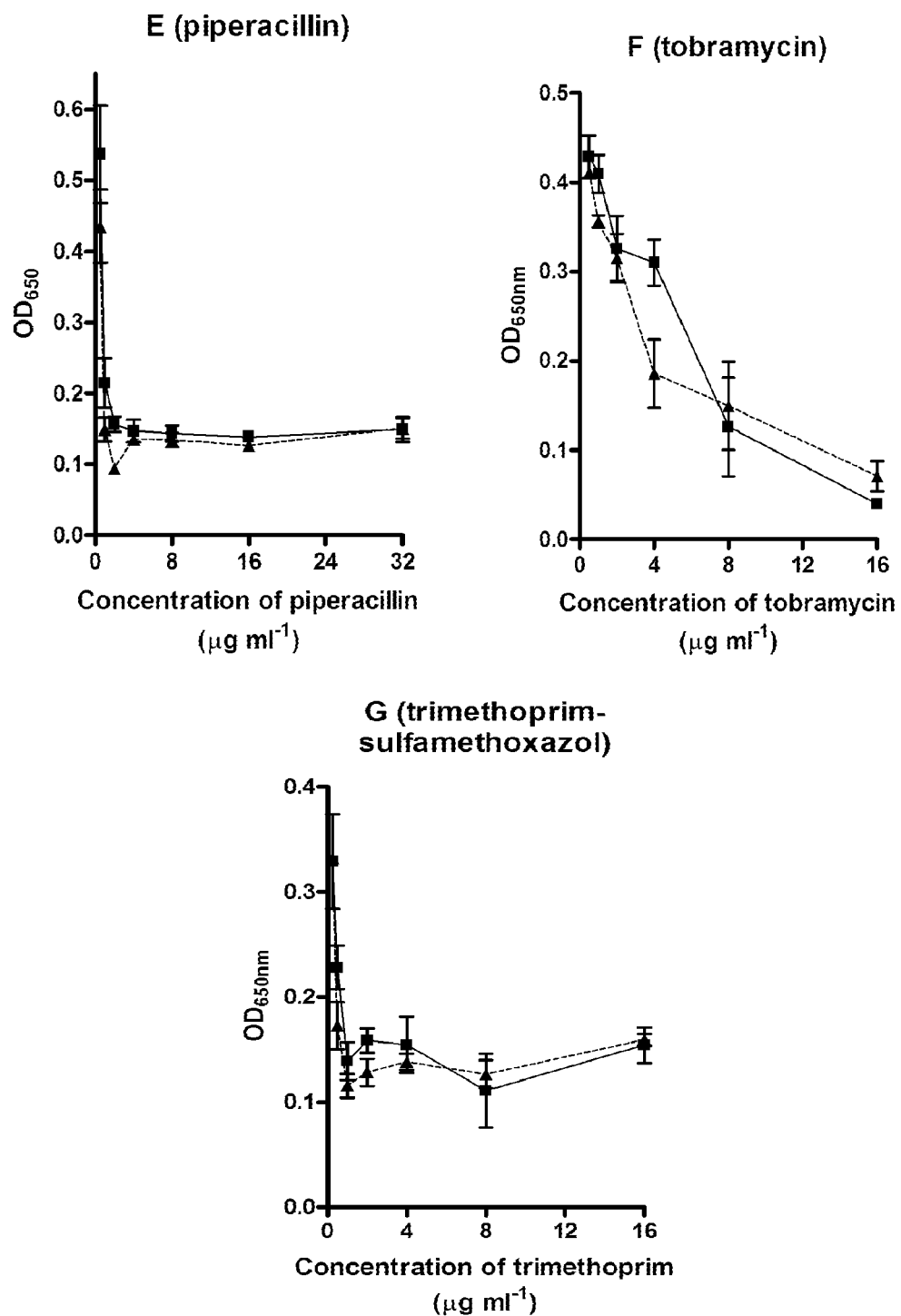
Figure 23/cont.

| n | Surfactin | Molecular weight |
|---|---|---|
| 8 | C13 | 1008 |
| 9 | C14 | 1022 |
| 10 | C15 | 1036 |

R = Alanine  Fengycin A
R = Valine  Fengycin B
n = 10-13

| n | Fengycin type | Molecular weight |
|---|---|---|
| 10 | C14-Fengycin A | 1435 |
| 11 | C15-Fengycin A | 1449 |
| 12 | C16-Fengycin A | 1463 |
| 13 | C17-Fengycin A | 1477 |
| 10 | C14-Fengycin B | 1463 |
| 11 | C15-Fengycin B | 1477 |
| 12 | C16-Fengycin B | 1491 |
| 13 | C17-Fengycin B | 1505 |

BIOSURFACTANT COMPOSITION PRODUCED BY A NEW *BACILLUS LICHENIFORMIS* STRAIN, USES AND PRODUCTS THEREOF

This application is the U.S. national phase of International Application No. PCT/IB2009/055334 filed 25 Nov. 2009 which designated the U.S. and claims priority to International Application No. PCT/IB2008/003583 filed 10 Dec. 2008, the entire contents of each of which are hereby incorporated by reference.

FIELD OF THE INVENTION

The present disclosure concerns a new *Bacillus licheniformis* strain, a biosurfactant composition produced by such a bacterial strain, as well as uses of such a biosurfactant composition and products containing such a biosurfactant composition in association with biocides in industrial and medical field.

BACKGROUND OF THE INVENTION

A biofilm is a community of microorganisms attached to a surface, surrounded by an extracellular polymeric substance (EPS) made of polysaccharides, DNA and proteins, able to protect microbes from environmental assaults. Bacterial attachment to surfaces and consequent biofilm formation are known phenomena in diverse environments such as medical and food industry devices.

Bacteria growing as a biofilm remain a significant challenge as they tend to be more tolerant to antimicrobial treatments.

Biofilms are an important cause of infections associated with biomaterials and urinary tract infections (UTIs) and are an important cause of nosocomial infections with significant morbidity, mortality and additional hospital costs.

Intact host defence systems usually eliminate transient bacterial contamination or colonization, but the presence of foreign bodies, such as catheters and implants, lowers the threshold of bacterial sustainable infection and generates local immunosuppression allowing biofilm formation on foreign surfaces in the human body, that tends to be recalcitrant to standard antimicrobial treatment. The biofilm formation can, in fact, immediately start once a biomedical device has been placed in its body niche. As frequent replacement of the prosthesis due to bacterial infection is uncomfortable, costly, time consuming and may lead to damage of the cellular tissue of patients, alternative approaches to catheter infection treatments must be found. Approximately 80% of nosocomial UTIs are associated with the use of indwelling urinary catheters and UTIs are responsible for 40-60% of all hospital-acquired infections. Bacteria found adhering to the intraluminal surfaces of catheters are the principal source and cause of bloodstream infections. Approximately five million central venous catheters are inserted per year, and of these 3-8% lead to bloodstream infection. The attributable mortality of these bloodstream infections is 12-25%. In contrast, the mortality rate of catheter-associated UTI is less than 5%. *Escherichia coli* is one of the most prevalent pathogens in UTIs such as prostatitis in adult men and cystitis in women.

Biofilm infection and its correlated diseases can be limited by preventing microbial adhesion to tissues and/or medical device surfaces but also an effective therapy to eliminate an existing biofilm is desirable.

Biosurfactants, amphiphilic metabolites produced by a wide group of bacteria from various biochemical building blocks, can be a useful approach to challenge bacteria growing as a biofilm. Microbial biosurfactants include a wide variety of surface-active compounds such as glycolipids, lipopeptides, polysaccharide-protein complexes, phospholipids, fatty acids and neutral lipids. Among the many classes of biosurfactants, lipopeptides (surfactin, iturin and fengycin classes) are particularly interesting because of high surface activity and antibiotic potential.

surfactin is a mixture of cyclic lipopeptides built from variants of a heptapeptide and a β-hydroxyl fatty acid with chain length of 13-15 carbon atoms. It is produced by various *Bacillus* strains. A lactone bridge between the β-hydroxyl function of the acid and the carboxy-terminal function of the peptide confers a cyclic structure to this molecule. A natural diversity occurs, giving rise to homologues differing from each other by the acyl chain length (13 to 15 atoms of carbon) and further isoforms are characterized by differences in the amino acid sequence.

fengycin family consists of a β-hydroxy fatty acid connected to the N-terminus of a decapeptide, including four D-amino acid residues and the rare amino acid L-ornithine. The C-terminal residue of the peptide moiety is linked to the tyrosine residue at position 3, forming the branching point of the acylpeptide and the eight-membered cyclic lactone. fengycin consists of two isoforms, fengycin A and B, which differ in their amino acid sequences. fengycin A presents Ala at position 6, fengycin B presents Val at the same position. The length of the β-hydroxy fatty acid tail is variable (from $C_{14}$ to $C_{18}$) and links the amino group of its N-terminal amino acid Glu. Different homologous compounds for each lipopeptide family are thus usually coproduced by the same bacterial strain.

Biosurfactants have advantages over their synthetic chemical counterparts because of their biodegradability and reduced toxicity, availability from cheap raw materials, biocompatibility and the effectiveness at extreme temperature, pH and salinity. Biosurfactants have found possible applications in biomedical fields.

Organisms within a biofilm are difficult to eradicate by conventional antimicrobial therapy and can cause indolent infections. Resistance of bacterial infections to antibiotics is increasing worldwide and some older antimicrobial agents are no longer recommended because of high levels of resistance.

Antibiotics and biocides may kill the free-living microorganisms (planktonic), but are not fully effective in killing organisms in a biofilm, leaving viable cells on surfaces. EPS confers protection from cellular immunity, by preventing phagocytosis, and from antibiotics. In addition, biofilms show increased resistance to antibiotics by decreasing antibiotic penetration through EPS, upregulating multi-drug efflux pump expression and expressing periplasmic glucans that directly bind to and sequester antibiotics.

Bacteria in deep biofilm layers can be less metabolically active, compared with their planktonic counterparts and, thus, appear to be more resistant to antibiotics. Bacteria living in a biofilm can create self-generated diversity that insures the survival of microorganisms sharing enzymes and proteins produced by other community members.

Several attempts have been made to avoid biofilm formation by incorporation of biocides into surface materials or by coating surfaces with biocides, especially in the medical field. It has been suggested that strategies for antimicrobial use in UTIs should be based on more potent antimicrobial agents, not necessarily broader-spectrum agents, and appropriate dosage and duration of antibiotic treatment.

SUMMARY OF THE INVENTION

The need is therefore felt for the identification of new compositions effective against different biofilm and planktonic bacterial strains, in order to prevent microbial colonization and growth, on abiotic and biotic surfaces.

The object of this disclosure is providing such compositions.

According to the invention, the above object is achieved thanks to the subject matter recalled specifically in the ensuing claims, which are understood as forming an integral part of this disclosure.

An embodiment of the present disclosure provides a new *Bacillus licheniformis* strain named V9T14 (deposited by Marcopolo Engineering S.p.A. with the Deutsche Sammlung von Mikroorganismen und Zellkulturen on Jan. 10, 2008 with accession number DMS 21038) and a new biosurfactant composition effective against different biofilm and planktonic bacterial strains produced by such new *Bacillus licheniformis* strain.

A further embodiment provides the use of such a biosurfactant composition, optionally in combination with at least one biocide, to prevent the colonization and/or biofilm formation from bacteria on abiotic surfaces, like medical device surfaces, hospital surfaces and/or food industry surfaces.

A further embodiment of the present disclosure concerns the biosurfactant composition, optionally in association with at least one biocide, for the prevention and/or treatment of an infection caused by bacteria able to grow planktonically and/or as a biofilm. The biosurfactant composition, optionally in association with at least one biocide, is suitable for topical administration to a patient, in particular is suitable for skin and/or mucosa application.

A further embodiment provides a product containing the biosurfactant composition and at least one antibiotic as a combined preparation for simultaneous, separate or sequential use for the prevention and/or treatment of an infection caused by bacteria able to grow planktonically and/or as a biofilm, preferably on biotic surfaces.

In a still further embodiment, the present disclosure concerns a device, preferably biomedical device to be inserted and/or implanted in a human or animal body, comprising on its surfaces the biosurfactant composition, optionally in combination with at least one biocide. Devices of this type can be catheters, implants, prostheses, etc.

BRIEF DESCRIPTION OF THE DRAWINGS

The invention will now be described, by way of example only, with reference to the enclosed figures of drawing, wherein.

DETAILED DESCRIPTION OF EXEMPLARY EMBODIMENTS

Figure 1:
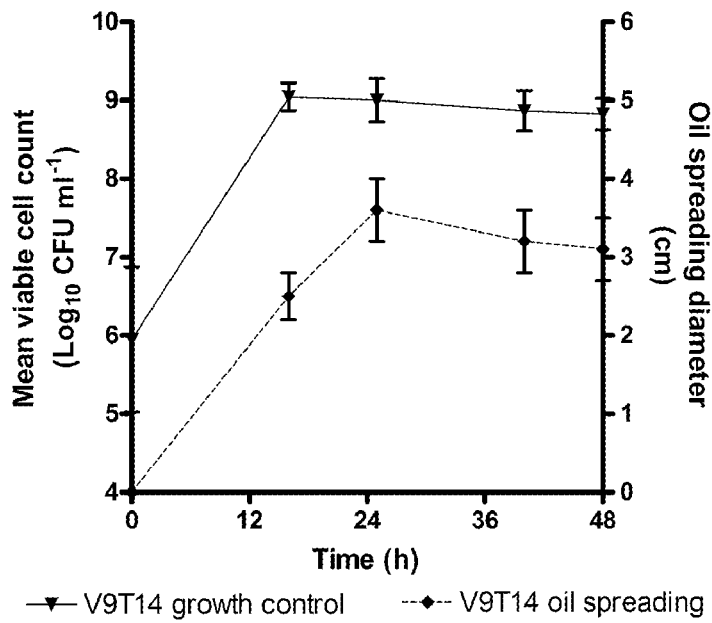
FIG. 1. Growth and culture supernatant oil displacement diameter of *B. licheniformis* V9T14. The strain was grown in Luria Bertani broth (LB) at 28° C. Oil spreading diameters were measured after removal of cells by centrifugation. Values are average for three cultures.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

This disclosure shows that a biosurfactant producer belonging to *Bacillus licheniformis* group, isolated and purified from an organic ammendant, is able to produce very efficient and effective biosurfactant.

The new *Bacillus licheniformis* strain named V9T14 was isolated from the organic ammendant Enzyveba Nucleobase 2 (EN2) commercialized by Marcopolo Engineering S.p.A. and was deposited with the Deutsche Sammlung von Mikroorganismen und Zellkulturen on Jan. 10, 2008 with accession number DMS 21038 in accordance with Budapest Treaty.

Monitoring the surface tension during growth of V9T14, the present inventors observed that biosurfactant was produced at the end of the exponential phase. V9T14 growth was observed both at 5% and 10% NaCl but less at 10%, however, biosurfactant was produced only up to 5%.

V9T14 produced a biosurfactant that showed a good effectiveness and efficiency, defining effectiveness as the lowest value to which the surface tension can be reduced and efficiency as the concentration required to reach the critical micelle concentration (CMC) value.

The biosurfactant composition produced by V9T14 strain comprises surfactin and fengycin as witnessed by infrared spectra analysis and mass spectrometry analysis. The infrared spectra analysis conducted on V9T14 biosurfactant confirmed that this substance was lipopeptide compound. Mass spectrometry analysis of V9T14 biosurfactant showed principally two groups of molecules, belonging to surfactin and fengycin metabolites and differing for homologue and isoform compositions. surfactin group represents about 70-84% by weight of the biosurfactant composition and fengycin group represents about 16-30% by weight.

surfactin family showed three main homologues (MW 1008, 1022, 1036) that differ for the length of fatty acid chain, $C_{13}$, $C_{14}$ and $C_{15}$, respectively. If the areas under the peaks eluted between 16 and 22 min (FIG. 18) are summed to give the total surfactin peak areas for the surfactin family of V9T14 biosurfactant, a relative surfactin content $C_{13}:C_{14}:C_{15}$ ratio range of 15-29%:9-23%:54-69% is obtained. These data compared with commercial surfactin (Sigma) revealed different relative abundances of these main homologues, wherein the relative surfactin content $C_{13}:C_{14}:C_{15}$ ratio (Sigma standard) is equal to 1%:50%:49%.

Results obtained by ESI-MS/MS on fengycin molecules showed the presence of precursor ions and product ions with m/z similar to those observed by Wang et al. (2004); it is possible to deduce that the molecules at MW 1477 and 1505 present in V9T14 biosurfactant are as $C_{17}$ fengycin A and $C_{17}$ fengycin B, respectively.

Results obtained by HPLC-MS/MS showed many fengycin lipopeptides of families A and B. Regarding retention times, molecular weight and product scan ions fengycin lipopeptides are divided in their families. fengycin relative composition of family A and family B inside biosurfactant V9T14 shows that $C_{17}$ fengycin A and $C_{17}$ fengycin B represent the more abundant homologues inside their families. More specifically, $C_{17}$ fengycin A is present in an amount in the range 15-35% by weight and $C_{17}$ fengycin B is present in an amount in the range 45-65% by weight with respect to the total weight of the composition fengycin molecules.

The present disclosure showed, then, that NaCl concentration inhibited the production of surface active agents from *B. licheniformis* V9T14 at 10% NaCl. Extracted V9T14 biosurfactant showed high stability at NaCl concentration up to saturation, with its maximum activity at salt saturation. Moreover, the biosurfactant had high stability over a wide range of pH (from 5 to 11), reaching the maximum surface activity at pH 5.

The surface tension of an aqueous solution of this biosurfactant composition reached 26 mN/m at 500 µg/mL. At CMC value, surface tension was about 30 mN/m.

Because biofilm formation by hazardous bacteria on biotic and abiotic surfaces is a serious and sometimes life-threatening problem the biosurfactant V9T14 has very interesting properties to reduce the hazardous effects of biofilms.

The present disclosure, thus, provides demonstration that such a biosurfactant composition, optionally combined with at least one biocide, is suitable for preventing and/or treating infections caused by bacteria able to grow both planktonically and/or as a biofilm on surfaces of abiotic (i.e. artificial surfaces) and biotic types (i.e. animal or human tissues).

The biosurfactant composition, optionally combined with at least one biocide, can be applied (optionally as a coating) to a surface in any of liquid, powder, solid, semisolid and/or gaseous forms. The term "gaseous" means any form like vapour, gas, volatile. The term "semisolid" means any form like cream, paste, gel, etc.

The biosurfactant composition, optionally combined with at least one biocide, can be applied (optionally as a coating) to the surfaces of medical devices as, for example, catheters, implants, prostheses, hip prostheses, knee joint prostheses, spinal column implants, osteosynthesis implants, orthopaedic implants, dental implants, breast prostheses, reconstructive implants, vascular prostheses, catheter chambers, gastric balloons, gastric rings, gynaecological devices, intracranial clips.

The biosurfactant composition, optionally combined with at least one biocide, can also be applied topically on skin and/or mucosa of a patient. Such a composition can be in the form of gel, cream, ointment, lotion, spray, salve, ophthalmic drop, ear drop, irrigation fluid, shampoo, or can be directly applied to bandages, plasters, etc. for the treatment of the skin and/or mucosa of a patient suffering of a bacterial infection.

With the term "biocide" is meant a chemical substance capable of killing living organisms, usually in a selective way. Some substances used as biocides are also employed as antifouling agents or disinfectants under other circumstances: chlorine, for example, is used as a short-life biocide in industrial water treatment but as a disinfectant in swimming pools. Many biocides are synthetic, but a class of natural biocides, derived from e.g. bacteria and plants, includes *brassica oleracea, brassica oleracea gemmifera*, and *clostridium botulinum* bacteria. To the class of biocides belong antimicrobial agents like germicides, antibiotics, antibacterials, antivirals, antifungals, antiprotozoals and antiparasites.

The present disclosure showed the effects of the biosurfactant composition produced by the new V9T14 strain on i) inhibition of biofilm formation and ii) removal of bacterial colonization from polystyrene surfaces.

The extent of adhesion of four microbial strains on polystyrene in the presence or absence of the V9T14 biosurfactant was analyzed using the Calgary Biofilm Device under shear forces. The results obtained by precoating of the pegs prior to inoculation showed that this was just as effective as including biosurfactant in the growth medium. A reduction of 97% was observed for biosurfactant V9T14 against *E. coli* CFT073.

V9T14 lipopeptide biosurfactant can inhibit biofilm formation through binding to cell surfaces or to cell surface components, thereby influencing the outer membrane hydrophobicity.

This is the first time that the biosurfactant fengycin has been demonstrated to be able to prevent adhesion of the biofilm produced by a pathogenic *E. coli* since its activity until now has been shown only against planktonic *E. coli* and mainly against phytopathogenic fungi.

A synergistic activity of several antibiotics associated with V9T14 biosurfactant was demonstrated in the present disclosure as a highly effective biofilm eradication approach. In the case of planktonic cells, the results demonstrated an increase of bactericidal activities in the presence of biosurfactant at low concentration of ampicillin, cefazolin and ceftriaxone, followed by a rapid decline leading to complete killing of all microbial cells as the concentration was increased. Ciprofloxacin and trimethoprim/sulphamethoxazol showed a decrease of planktonic bacterial viable cell count as well, yet complete eradication was not obtained under the conditions explored. For each of these antibiotics, with the exception of cefazolin, growth inhibitory effects were not modified. Bactericidal action of tobramycin, the only aminoglycoside tested, against planktonic forms does not seem to be influenced by the presence of V9T14 biosurfactant. While the inhibitory efficacy was increased, the MIC of cefazolin was reduced from 16 to 8 µg/mL.

In the case of adherent biofilm cells, complete eradication was observed for the association of V9T14 biosurfactant with ampicillin. Reduction of biofilm population ranging from 0.5-1.7 log was observed with all the other antibiotics tested. The concentration of antibiotics associated with biosurfactant was decreased to obtain the same cell reduction observed using the antibiotic alone.

V9T14 biosurfactant action lies in its interaction with biofilm EPS and bacterial membranes, increasing the activity of antimicrobial agents by forming pores in the outer membrane and by facilitating the entrance of antibiotics through the EPS of the biofilm.

The present disclosure demonstrates that the co-administration of V9T14 biosurfactant with different antibiotics led to a strong positive synergy between the two molecules in biofilm cell eradication. The effect was that for the majority of antibiotics tested the $MBEC_{99.9\%}$ was decreased significantly. Also, the bactericidal effect on planktonic cells ($MBC_{99.9\%}$) was influenced by the presence of the two agents together, while the MIC seemed unaffected for the majority of antibiotics tested.

The present disclosure, further, demonstrates that the co-administration of V9T14 biosurfactant with silver, copper and quaternary ammonium compounds (exemplary compounds of inorganic biocides) led to a strong positive synergy between the two molecules in biofilm cell eradication of different microorganisms. V9T14 biosurfactant reduces the "restricted penetration" of metals through the EPS, increasing metal concentration in the core of the biofilm. In addition, V9T14 interacts with the bacterial membrane forming pores and altering the membrane integrity, allowing for $Ag^+$ or $Cu^{2+}$ to more freely penetrate the cell. Moreover, the presence of the negatively charged amino acids ring limits the interaction between metal ions and the EPS. This could lead ultimately to an increase of metal entrance into the EPS and the outer membrane of bacterial cells, enhancing the activity of metal ions.

The presence of V9T14 biosurfactant increases the efficacy of silver ions in biofilm killing and reduces biofilm population below the detection limit. Concentration of silver in the solution containing V9T14 biosurfactant and silver needed to obtain this reduction in *E. coli* CFT073 biofilm was 258-fold less that the concentration of silver alone. The present inventors also observed that the combination of silver and V9T14 completely killed planktonic cells after 24 h at a concentration 64-fold less than that of silver alone. The present data also further confirm that exposure time plays a key role in biofilm removal.

This is the first time that a synergistic interaction between silver and a lipopeptide biosurfactant was observed. Therefore, the activity of silver and V9T14 biosurfactant is useful in disinfection of surfaces to reduce bacterial colonization and consequent spreading of diseases.

Materials and Methods
Isolation, Culture Conditions and Biosurfactant Screening

The strain V9T14 was isolated from the organic ammendant Enzyveba Nucleobase 2 (EN2) (Marcopolo Engineering S.p.A, Borgo San Dalmazzo, Italy). Morphological characteristics were defined by observation at the stereomicroscope and performing Gram staining on an overnight culture on $NA+Mn^{2+}$ media. Identification was performed by using the GP-ROD-SB BIOLOG® assay (Microlog, U.S.A). The V9T14 strain was stored at −80° C. in LB broth (Fluka) supplemented with 30% glycerol. The isolate V9T14 was deposited by Marcopolo Engineering S.p.A. with the Deutsche Sammlung von Mikroorganismen und Zellkulturen with accession number DMS 21038 on Jan. 10, 2008 in accordance with Budapest Treaty.

For biosurfactant screening, one colony of an overnight culture of the strain V9T14, grown on LB agar at 28° C., was inoculated into 10 mL of LB broth. Cultures were incubated on a rotatory shaker at 200 rpm for 24 h at 28° C. Thereafter, cell suspension was centrifuged at 10000×g for 5 min and the supernatant was assayed for the presence of surfactant by using the oil spreading method as disclosed in Morikawa et al. (2000).

Amylase and Cellulase Production

To determine the amylase production, the V9T14 strain was grown on a Petri dish containing M9 agar medium added with 0.5% starch (Waldeck et al., 2007). After incubation, plates were overlayed with Lugol solution. For cellulase production, the strain was grown on a Petri dish containing M9 agar medium added with 0.5% carboxymethyl cellulose. Plates were incubated at 28° C. for 24 and 48 h. After incubation, plates were overlayed with Congo red solution (0.1% w/v). Enzyme production was estimated by measuring the area of the halos around a single colony.

Oil Spreading

Oil spreading assay (Morikawa et al., 2000) was performed by using 20 μL of Motor Oil 10W-40 (Selenia) previously deposited onto the surface of 20 mL of distilled water in a Petri dish (90 mm in diameter) to form a thin membrane. Twenty microliters of bacterial supernatant were gently put onto the centre of the oil membrane. Diameters of clearly formed oil displaced circles were measured to determine the presence of biosurfactants.

Bacterial Halotolerance and Biosurfactant Production

The V9T14 strain was inoculated in LB broth with 50 and 100 g/L of NaCl and incubated at 28° C. for 48 h. Bacterial growth was monitored at $OD_{595\ nm}$, biosurfactant production was estimated by the measurement of the surface tension assessed with a Sigma 703D tensiometer (KSV) equipped with a du Nouy platinum ring.

Biosurfactant Extraction and Enrichment

For biosurfactant production, seed culture was prepared by transferring a loop of the V9T14 strain from a LB agar overnight culture into 10 mL of LB broth and incubated at 28° C. for 4 h at 200 rpm. Thereafter, 2 mL were inoculated in 500 mL of LB broth in a 2000 mL flask and incubated again at 28° C. for 24 h at 120 rpm. The overnight liquid culture was centrifuged at 8000×g for 30 min and the supernatant was collected. Bacterial pellet was resuspended in distilled water and centrifuged again at 8000×g for 30 min. Supernatants were pooled, acidified to pH 2 with 6 N HCl, stored at 4° C. overnight and extracted with ethyl acetate/methanol (4:1) three times. The organic fraction was evaporated to dryness under vacuum condition, acetone was added to recover the raw biosurfactant. Acetone was evaporated and the biosurfactant was collected and weighed. Within the present disclosure, the term V9T14 refers to the extracted V9T14 biosurfactant.

Surface Tension and Critical Micelle Concentration

To measure the surface tension between biosurfactant solution and air, a purified biosurfactant solution was prepared in alkaline sterile demineralized water at 500 μg/mL. Measurement was carried out at 24° C.±0.5 in triplicate with a K10 tensiometer (Krüss GmbH, Hamburg, Germany) equipped with a du Nouy platinum ring. Distilled water was used for calibration. Twenty milliliters of biosurfactant solution were used for each measurement; the ring was placed just below the surface of the solution, subsequently the force to move this ring from the liquid phase to the air phase was determined in triplicate.

Critical Micelle Concentration (CMC) was determined on serially diluted biosurfactant solutions in alkaline distilled water. Surface tension of each dilution was determined in triplicate. Maximal standard deviation admitted to surface activity measurements was 0.30 mN/m. The CMC of the biosurfactant was estimated from the intercept of two straight lines extrapolated from the concentration-dependent and concentration independent sections of a curve plotted between biosurfactant concentration and surface tension values.

Stability Studies

The effect of different parameters on the surface activity of the extracted biosurfactant produced by V9T14 strain was determined. Solutions of extracted biosurfactant were prepared in distilled water at 100 µg/mL (final pH adjusted to 7.0 with 1 N NaCl) containing different concentrations of NaCl ranging from 0% to saturation (about 35%) and the surface tension was measured. The pH of the purified biosurfactant water solutions was adjusted to different values, ranging from 2.3-10.3, using 3 N NaOH or 3 N HCl and surface tension was measured. Each measure was made in triplicate and the average and standard deviation were calculated.

FT-IR Spectrometric Analyses

Fourier Transform Infrared (FT-IR) absorption spectrometry was used to define the structure of V9T14 biosurfactant. FT-IR spectra were obtained with a Thermo Nicolet Avatar 370 FT-IR spectrometer equipped with a diffuse reflectance accessory. One milligram of the sample was mixed thoroughly with 100 mg of homogenised porcelain-milled KBr (FT-IR grade). A pellet was prepared using a press. The pellet was immediately put into the sample holder and FT-IR spectra were recorded. Data were collected and processed with Ez Omnic software. FT-IR scanning was conducted in ambient conditions. The resolution was set to 4 $cm^{-1}$ and the operating range was 500-4000 $cm^{-1}$. Sixty-four spectra per sample were recorded, averaged for each spectrum and corrected against the spectra of pure KBr and ambient air as background.

Thin-layer Chromatography

Analytical thin-layer chromatography (TLC) was carried out on pre-coated silica gel 60 $F_{254}$ plates (Merck Co. Inc, Damstadt, German). TLC plates were spotted with the sample extracted biosurfactant dissolved in methanol and developed using the following mobile phase: methanol:chloroform:acetic acid, 89:9:2, by vol. (1) and chloroform:methanol:water, 65:25:4 by vol. (2). Substances were visualized by spraying chromatograms both with non specific reagent (such as 4% potassium permanganate followed by charring at 170-180° C.) and with reagents specific to detecting peptides and free amino groups (such as with 2% ninhydrin solution in butanol followed by heating at 110° C.).

Silica Gel Chromatography

The V9T14 biosurfactant extract (150 mg), purified according the method previously described, was chromatographed on a column of silica gel (0.046-0.066 µm; Merck KGa) (40 g). Elution was carried out with chloroform and then with chloroform-methanol mixture with the methanol concentration gradually increased from 10% to 100%. The process was monitored by TLC in solvent system (1). Five main samples (A-E) have been collected and successively analyzed by MS and HPLC/MS. Two main samples are reported: sample B (42.9 mg) and sample D (33.8 mg).

Determination of the Lactone Bond

To determine the lactone linkage 1 mg of lipopeptides of sample D was dissolved in 1 M potassium hydroxide (KOH) solution and allowed to react overnight at room temperature. Excess KOH was neutralized and the hydrolysate was desalted for mass spectrometry analysis.

Mass Spectrometry Analysis

An aliquot of V9T14 biosurfactant dried material was dissolved in methanol/acetonitrile (50/50 v/v) to obtain a 1000 µg/mL stock solution. Freshly prepared intermediated stock solutions were made by diluting the stock solution with methanol/water (50/50 v/v) to 15 µg/mL solutions.

All mass spectrometry analyses were performed using a LCQ DECA XP Plus (Thermo Finnigan, San José, USA) Ion Trap mass instrument equipped with an electrospray ion source. Samples (15 µg/mL solutions) were infused with a syringe. The electrospray source was operated, respectively, at a capillary voltage of 21 V and a spray voltage of 5.3 kV in positive ion mode, and at 15 V and −5 kV in negative ion mode; capillary temperature was set at 350° C. MS full scans in positive and negative ion modes in the range 100-2000 m/z were acquired. ESI-MS/MS analysis was also used. The target ionized molecules or sodium-ionized molecule were selected and then fragmented and the product ions were recorded.

Liquid Chromatography-Mass Spectrometry Analysis

A Surveyor HPLC coupled on line to a LCQ DECA XP Plus (Thermo Finnigan, San José, USA) Ion trap mass spectrometer equipped with an electrospray ionization source (ESI) was employed. Separations were performed using a precolumn: (Security guard cartridges) $C_{18}$ Phenomenex 4 mm×3.0 mm and a column: $C_{18}$ Luna, Phenomenex, 150 mm×4.5 mm, 5 µm. The mobile phase components were: A=water, 1% formic acid; B=acetonitrile; the lipopeptides were eluted according to the following linear gradient: A:B (50:50) for 3 min, then A:B (0:100) over 18 min and then 100% B over 5 min at a flow rate of 0.8 mL/min; MS full scan positive and negative ion modes in the range 100-2000 m/z were performed; alternatively ESI-MS/MS was applied to the selected precursor ions.

Biosurfactant Stock Solution for Biological Assays

V9T14 biosurfactant was dissolved in PBS (pH 7.2) at the final concentration of 5120 µg/mL and the final pH was adjusted to 7.0 by using 6 N NaOH or 6 N HCl. These solutions were filtered through 0.2 µm filters and then stored at 4° C. Stock solutions of V9T14 biosurfactant were diluted at a ratio of 1:1 in PBS.

Biocides.

The term biocide includes any chemical substance capable of killing living organisms. Within the present disclosure biocides are to be considered including antibiotics, antibacterials, germicides and also inorganic compounds having the ability of killing at least bacteria.

The inorganic compounds encompassed in the present disclosure with the term biocide can be i.e. Sodium selenite ($Na_2SeO_3$; Sigma Chemical Company, St. Louis, Mo.), silver nitrate ($AgNO_3$; Sigma), cupric sulfate ($CuSO_4.5H_2O$; Fischer Scientific, Ottawa, Ontario, Canada), zinc sulfate ($ZnSO_4.7H_2O$; Fischer Scientific), and aluminum sulfate [$Al_2(SO_4)_3.18H_2O$; Fischer Scientific).

The antibiotics encompassed in the present disclosure are i.e. ampicillin, cefazolin, ciprofloxacin, ceftriaxone, tobramycin and trimethoprim/sulfamethoxazol.

Other biocides advantageously used in combination with the biosurfactant composition of the present disclosure are Polycide (Pharmax Limited, Toronto, Ontario, Canada), Virox (Virox Technologies Incorporated, Oakville, Ontario, Canada), Stabrom 909 (Albemarle Corporation, Richmond, Va.), isopropyl alcohol (Sigma), benzalkonium chloride (alkyldimethylbenzyl ammonium chloride; Sigma), cetalkonium chloride(cetyldimethylbenzyl ammonium chloride; FeF Chemicals, Denmark), cetylpyridinium chloride (cetyldimethylpyridyl ammonium chloride; FeF Chemicals), and myristalkonium chloride(tetradecyldimethylbenzyl ammonium chloride; FeF Chemicals).

Stock Solutions of Metals and Biocides

Polycide (Pharmax Limited, Toronto, Ontario, Canada) was diluted in PBS to 2.5% (13250 ppm benzalkonium chloride) (2× the recommended concentration suggested by the manufacturer). Metals were dissolved in double distilled water (ddH$_2$O). AgNO$_3$ (Sigma) was dissolved in ddH$_2$O to 150 mM; CuSO$_4$ (Fischer Scientific Ottawa, Ontario, Canada) was dissolved in ddH$_2$O to a final concentration of 500 mM.

All solutions were sterile filtered and stored at 4° C. Antibiotics were diluted in ddH$_2$O at the final concentration of 1024 μg/mL. Working concentrations for antibiotics and biocides are summarized in Table 1. Serial two-fold dilutions were performed to create the challenge plate (see below).

TABLE 1

| Chemical agents | Exposure time | Dilution medium | Working concentration |
|---|---|---|---|
| Polycide | 30 min | PBS | 2.5% |
|  | 2 h-8 h | MSVG |  |
| Ag$^+$ | 24 h |  | 15 mM |
| Cu$^{++}$ | 2 h-8 h | MSVG | 50 mM |

Bacterial Biofilm

Biofilms were grown in the Calgary Biofilm Device (CBD, Innovotech, Edmonton, AB, Canada) as described by Harrison et al. (2006). The CBD consists of a polystyrene lid with 96 pegs that may be fitted inside a standard 96-well microtiter plate. Each peg of the CBD has a surface area of approximately 109 mm$^2$. For the anti-adhesion experiments, frozen stocks of four bacterial pathogens were used.

E. coli CFT073 was streaked on LB agar, S. aureus ATCC 29213 and P. aeruginosa PA14 on TSA and the isolate S. epidermidis on Cathion-Adjusted Mueller-Hinton agar and all incubated overnight at 37° C. A second fresh subculture of each microbial strain was grown overnight at 37° C. on the appropriate agar medium. Using a cotton swab, colonies from this fresh secondary subculture were suspended in the respective broth medium to match a 1.0 McFarland standard, corresponding to approximately 3.0×10$^8$ cfu/mL. This suspension was diluted again 30-fold in broth to create the inoculum for the CBD, that was approximately 1.0×10$^7$ cfu/mL. Then, 150 μL of the bacterial inoculum were added to each well of a 96-well microtiter plate. The CBD peg lid was then fitted inside of this and the assembled device was placed on a gyrorotary shaker at 150 rpm in a humidified incubator for 24 h. Following the period of incubation, biofilms were rinsed twice by inserting the peg lids into microtiter plates with 200 μL/well of 0.9% saline for 2 min to remove loosely adherent cells.

For coating experiments, the CBD was previously coated with biosurfactant by dipping the lid of the CBD into 200 μL of the stock solution and its dilutions previously put in each well of a microtiter plate. The CBD was incubated at 37° C. on a rotatory shaker at 125 rpm for 24 h, then removed from the microtiter plate and dried under the hood for 1 min before adding it to the bacterial inoculum.

In another set of experiments, the CBD was used uncoated and microbial inoculum was distributed in each well together with biosurfactant stock dilutions to reach concentration ranges from 1-20 μg/well (5-100 μg/mL) in the final volume of 200 μL.

Strains and Growth Media for Silver

All the microbial strains used in this work are summarized in Table 2. Strains were stored at −70° C. in Microbank vials (ProLab Diagnostic, Toronto, Canada) according to the manufacturer's directions. E. coli strains were grown in Luria Bertani agar (LB, EMD Chemicals Inc.), all the other microorganisms were cultivated in Tryptic Soy Agar (TSA, EMD Chemicals Inc.). All microorganisms were incubated for 24 h at 37° C. E. coli biofilms were cultivated in LB broth, all the other biofilms were grown in Tryptic Soy Broth (TSB, EMD Chemicals Inc.) and all serial dilutions were performed using 0.9% NaCl. Susceptibility testing of biocides was performed in phosphate buffered saline (PBS) or Minimal Salts Vitamins Glucose (MSVG) (Table 2).

According to Teitzel and Parsek (2003), MSVG contained 1 g/L (NH$_4$)$_2$SO$_4$, 0.06 g/L MgSO$_4$.7H$_2$O, 0.06 g/L CaCl$_2$, 0.02 g/L KH$_2$PO$_4$, 0.03 g/L Na$_2$HPO$_4$.7H$_2$O, 2.384 g/L HEPES, 1 mL of 10 mM FeSO$_4$ and 0.990 g/L glucose. The pH was adjusted to 6.5 and autoclaved. Then 1 mL of Trace Vitamins Solution (TVS) was added. TVS contained 20 mg/L biotin, 20 mg/L folic acid, 50 mg/L thiamine HCl, 50 mg/L D-(+)-calcium pantothenate, 1 mg/L vitamin B12 (cyanocobalamina), 50 mg/L riboflavin, 50 mg/L nicotinic acid, 100 mg/L pyridoxine HCl, 50 mg/L of p-aminobenzoic acid (PABA). TSV solution was sterile filtered (0.2 μm) and stored at 4° C. in the dark.

TABLE 2

| Strains | Mean biofilm cell density[a] (log$_{10}$ CFU/peg) |
|---|---|
| Entero hemorrhagic Escherichia coli (EHEC) |  |
| E. coli O157:H7 Uropathogenic Echerichia coli (UPEC) | 4.3 ± 0.2 |
| E. coli CFT073 Methicillin Sensible Staphylococcus aureus (MSSA) | 6.4 ± 0.4 |
| S. aureus ATCC 25923 (SA25923) Pseudomonas aeruginosa (PA) | 5.2 ± 0.3 |
| P. aeruginosa PA14 | 6.0 ± 0.5 |

[a]Starting cell density measurements were based on the means and standard deviations of the pooled, log-transformed data after 24 h of growth.

The strains tested are publicly available by the Department of Biological Sciences, University of Calgary, 2500 University Drive NW, Calgary AB T2N 1N4 Canada.

Viable Cell Counting

The effect of the V9T14 biosurfactant was assessed by determining the viable cell counts after biofilms had been rinsed as described above. The lid of the CBD was then inserted into 200 μL of LB broth added with 1% Tween 20 in the wells of a microtitre plate. Biofilms were disrupted from the peg surface using an Aquasonic 250T ultrasonic cleaner (VWR International, Mississauga, ON, Canada) for 10 min. The disrupted biofilm cells were serially diluted in 0.9% saline, and then plated onto LB agar. Agar plates were incubated for 24 h at 37° C. and then enumerated. Viable cell counts for planktonic cultures (i.e. starting inocula and planktonic forms after incubation) were similarly carried out by serial dilution in 0.9% saline, and then by plating onto agar as described for biofilm cells.

Susceptibility Testing with Combinations of Biosurfactant and Antibiotics

Antibiotics tested were ampicillin, cefazolin, ciprofloxacin, ceftriaxone, piperacillin, tobramycin and trimethoprim/sulfamethoxazol (19:1) used at concentrations starting from 2× MIC, alone and in combination with V9T14 biosurfactant. Antibiotics were serially diluted (log$_2$) using 0.9% saline in a 96-well microtiter plate, and then a solution of biosurfactant was added to each well to reach a final concentration of 5 μg/mL.

E. coli CFT073 biofilms were grown on the CBD at 37° C. for 24 h in a rotatory shaker at 130 rpm, as described above.

Then CBD lid was rinsed twice with 0.9% saline, exposed to the antibiotics and antibiotic plus biosurfactant microtiter plate and incubated at 37° C., 125 rpm for 24 h. After exposure, the CBD was removed and the 96-well microtiter plate was used to estimate minimal inhibitory concentration (MIC) and minimal bactericidal concentration ($MBC_{99.99\%}$) values. For MIC value, the plate was read using a spectrophotometer at 650 nm, MIC was defined as the lowest concentration not presenting turbidity; according to the guidelines of the American Clinical Laboratory Standards Institute, the minimum bactericidal concentration (MBC) is conventionally defined as a concentration of an antimicrobial agent that kills 3 $log_{10}$ cells of a bacterial culture (or 99.9% of the bacteria). In our experiments we used a more restrictive criterion, defining the $MBC_{99.99\%}$ value, defined as the lowest concentration of the antibiotic activity higher than 4 $log_{10}$ by viable cell count. Minimal biofilm eradication concentration ($MBEC_{99.9\%}$) was defined as the lowest concentration to eradicate 3 $log_{10}$ of the viable microorganisms in a biofilm.

Susceptibility Testing with Combinations of Biosurfactant and Biocides

*E. coli* CFT073 and *E. coli* O157:H7 were grown on Luria Bertani agar (LB, EMD Chemicals Inc.), *P. aeruginosa* PA14 and *S. aureus* were grown on TSB agar. Susceptibility testing of metals was performed in Minimal Salts Vitamins Glucose (MSVG) according to Teitzel and Parsek (2003), while Polycide susceptibility testing was performed in Phosphate Buffered Saline (PBS).

Extracted V9T14 biosurfactant was stored under the chemical hood providing solvent evaporation until dryness. The biosurfactant powder was homogenized using a porcelain mortar and a pestle. V9T14 was dissolved in PBS and pH was adjusted to 7.5 with 1 N NaOH. Volume was adjusted to match a final concentration of 5000 μg/mL.

$AgNO_3$ (Sigma) and $CuSO_4$ (Sigma) were dissolved in double distilled water ($ddH_2O$) to 150 mM and 500 mM respectively. Polycide was diluted in PBS to 25%. Solutions were sterile filtered and stored at 4° C. Working concentrations for metals and biocide are shown in Table 1. Serial two-fold dilutions were performed to create the challenge plate.

Biofilms were grown in the Calgary Biofilm Device (CBD) as described above. Starting from cryogenic stock, the strain was streaked out twice on TSA, and an inoculum was prepared by suspending colonies from the secondary agar subculture in 0.9% saline to match a 1.0 McFarland standard. This standard inoculum was diluted 1/30 in LB broth.

150 μL of this inoculum was transferred into each well of a 96-well plate, and the sterile peg lid of the CBD was inserted into the plate. The inoculated device was then incubated at 125 rpm, for 24 h at 37° C. and 95% relative humidity. In an alternative set of experiments, biofilms were grown for 48 h before silver exposure and spent medium was changed with fresh medium after 24 h.

Following this period of incubation, biofilms were rinsed once with 0.9% saline (200 μL/well) to remove loosely adherent planktonic cells. Biofilm formation was evaluated by breaking off four pegs from each device after it has been rinsed. Biofilms were disrupted from pegs into 200 μL/well of LB supplemented with 1% Tween 20 using an ultrasonic cleaner for a period of 10 min (Aquasonic model 250T, VWR Scientific, Mississauga, Canada) as described above. The disrupted biofilms were serially diluted in 0.9% saline and plated on LB agar for viable cell counting. An initial set of quality control assays were carried out to ascertain that the strain used in this study formed equivalent biofilm on the CBD pegs as described in Harrison (2008).

High-throughput Susceptibility Testing of Microbial Biofilms

The challenge plate of biocides, antibiotics and biosurfactant was made in a 96-well plate. Biocides were serially two-fold diluted in PBS and V9T14 biosurfactant was added to each well at the final concentration of 5 μL/mL. Antibiotics were similarly diluted in Muller-Hinton broth, while metals were diluted in MSVG. When prepared, each challenge plate had 7 sterility control, 8 growth control, 11 wells containing 5 μL/mL of V9T14 biosurfactant, 11 different concentrations of single biocide (or metals) and 11 different concentrations of biocide (or metals) associated with 5 μL/mL of V9T14 biosurfactant.

Biofilms that have been grown on lids of the CBD and rinsed once in 0.9% saline were inserted in the challenge plates. Following the exposure time at 37° C., biofilms were rinsed once with 0.9% saline (200 μL/well) and then placed in a microtiter "recovery" plate that contained 200 μL/well of neutralizing medium (TSB supplemented with 1% Tween 20, 2.0 g/L reduced glutathione, 1.0 g/L L-histidine, 1.0 g/L L-cysteine). The recovery plate was sonicated for a period of 10 min (Aquasonic model 250T, VWR Scientific, Mississauga, Canada). The disrupted biofilms were serially diluted in 0.9% saline and plated on the appropriate agar medium for viable cell counting. Plates were then incubated at 37° C. overnight and finally enumerated.

To define MBC of biocides, recovery plates were incubated at 37° C. for 24-48 h and the adsorbance ($OD_{650 nm}$) was read in a microtiter plate reader.

Confocal Laser Scanning Microscopy (CLSM)

Pegs were broken from the lid of the CBD using pliers (Harrison et al. 2006) and then rinsed once with 0.9% saline to remove planktonic forms. Prior to examination by CLSM, biofilms were fluorescently stained with acridine orange (AO) (Sigma Chemical Co., St. Louis, Mo., USA). To stain biofilms, pegs were immersed in 0.1% w/v AO in PBS for 5 min at room temperature in the dark. To determine live and dead cell distribution in antibiotic experiments, rinsed biofilms were stained with Syto-9 (6.7 μM) and propidium iodide (40 μM) (Live/Dead® BacLight™ Kit, Molecular Probes, Burlington, ON, Canada) at 30° C. for 30 min. Fluorescently stained biofilms were placed in two drops of 0.9% saline on the surface of a glass coverslip. These pegs were examined using a Leica DM IRE2 spectral confocal and multiphoton microscope with a Leica TCS SP2 acoustic optical beam splitter (AOBS) (Leica Microsystems, Richmond Hill, ON, Canada). To minimize or eliminate artefacts associated with single and/or simultaneous dual wavelength excitation, all dual labelled samples were sequentially scanned, frame-by frame, first at 476 or 488 nm and then at 543 nm. Fluorescence emission Δ was then sequentially collected in the green and red regions of the spectrum, respectively. Line averaging (×2) was used to capture images with reduced noise. A 63× water immersion objective was used in all imaging experiments. Image capture and two dimensional projections of z-stacks were performed using Leica Confocal Software (LCS, Leica Microsystems).

Interpretation of Results

The efficacy of biofilm adhesion inhibition was assessed by determining the minimal biofilm eradication concentration (MBEC) after 24 h by mean viable cell count. Each test was performed at least three times in triplicate on separate cultures.

The efficacy of antibiotics associated with V9T14 biosurfactant was assessed by determining the planktonic ($MBC_{99.99\%}$) and biofilm ($MBEC_{99.9\%}$) killing by mean viable cell count and the MIC value of antibiotics by absorbance at 650 nm, after 24 h of exposure. The difference attributed to synergy is expressed in Δ values between the $\log_{10}$ antibiotic cell count reduction and the $\log_{10}$ association value. "Eradication" was defined as no growth in antibiotic-free plates after planktonic culture initially incubated in antibiotic-containing LB broth.

Statistical Analysis

The Student's t test was performed when the aim was to investigate whether the difference in between the experimental values obtained under different conditions could be considered significant. To analyze the significance of the changes in the $\log_{10}$-transformed raw data, ANOVA statistical analysis was performed.

Results

Bacterial Isolation

EN2 had a earth-like texture with a culturable population on LB agar plates ranging from $9.1 \times 10^8$ to $1.6 \times 10^9$ cfu/g of dry ammendant. From these plates, more than 400 bacterial colonies were isolated. Forty-five isolates produced an hemolytic zone in blood agar within 24 h. All the isolates were grown in LB broth for 24 h and then tested for biosurfactant production with the oil spreading method. Fourteen biosurfactant-producing isolates were found and each of them showed large halos (more than 1 cm diameter). One isolate, V9T14 was selected for further study because of its ability to grow over a wide range of salinity, to show hemolysis and to produce efficient and effective extracellular biosurfactant, defining effectiveness the lowest value to which the surface tension can be reduced and efficiency the concentration required to reach the CMC value.

Strain Identification and Characteristics

Gram stain revealed that V9T14 was spore forming, Gram positive, rod. By using BIOLOG® system and conventional method for GP-ROD-SB identification, the strain V9T14 was identified as *Bacillus licheniformis* with the probability of 99%, a similarity of 0.639 and a distance of 5.49

Figure 8:
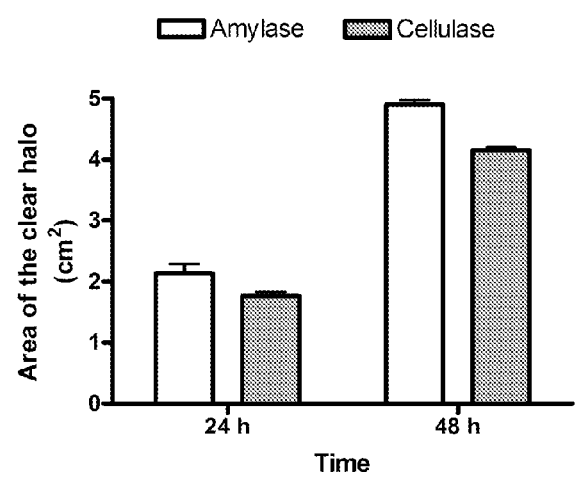
FIG. 8. Amylase and cellulase production at 28° C. after 24 and 48 h. Bacteria were grown on M9 agar minimal medium supplemented with 0.5% starch or carboxymethylcellulose. Area of the clear halo was measured after detection with Lugol solution or Congo red solution respectively.

Metabolic characteristics of *B. licheniformis* V9T14 are given in Table 3. The strain was able to produce amylase and cellulase at 28° after 24 and 48 h (FIG. 8). *B. licheniformis* V9T14 showed a high production of both enzymes.

TABLE 3

| Substrates | V9T14 |
| --- | --- |
| 2,3-butanediol | + |
| 2'-deoxy adenosine | + |
| 3-methyl glucose | + |
| Acetic acid | +/− |
| α-cyclodextrin | + |
| Adenosine | + |
| Adenosine-5'-monophosphate | − |
| α-D-glucose | + |
| α-ketoglutric acid | +/− |
| α-ketovaleric acid | +/− |
| α-methyl-D-glucoside | + |
| Amygdalin | +/− |
| Arbutin | + |
| β-cyclodextrine | + |
| β-methyl-D-glucoside | + |
| D-alanine | +/− |
| D-cellobiose | +/− |
| Dextrin | + |
| D-fructose | + |
| D-galactose | − |
| D-gluconic acid | + |
| D-lactic acid methyl ester | +/− |
| D-L-α-glycerol phosphate | − |
| D-mannitol | − |
| D-mannose | + |
| D-melezitose | + |
| D-psicose | + |

TABLE 3-continued

| Substrates | V9T14 |
| --- | --- |
| D-ribose | + |
| D-sorbitol | +/− |
| D-tagatose | − |
| D-trehalose | + |
| Gentiobiose | + |
| Glycerol | + |
| Glycil-L-glutamic acid | +/− |
| Glycogen | + |
| Inosine | + |
| Inulin | +/− |
| L-alanine | +/− |
| L-alanyl-glycine | +/− |
| L-arabinose | +/− |
| L-asparagine | +/− |
| L-glutamic acid | + |
| L-lactic acid | − |
| L-malic acid | +/− |
| L-serine | +/− |
| Maltose | + |
| Maltotriose | + |
| m-inositol | + |
| N-acetyl-β-D-mannosamine | +/− |
| N-acetyl-D-glucosamine | + |
| N-acetyl-L-glutamic acid | − |
| Palatinose | + |
| Pyruvatic acid methyl ester | +/− |
| Pyruvic acid | + |
| Salicin | + |
| Succinamic acid | +/− |
| Sucrose | + |
| Thymidine | + |
| Thymidine-5'-monophosphate | +/− |
| Turanose | + |
| Tween 40 | +/− |
| Uridine | + |

Colony appearance of the V9T14 strain is summarized in Table 4.

TABLE 4

| | V9T14 |
| --- | --- |
| LB agar | Shape: circular |
| | Edges: entire |
| | Elevation: pulvinate |
| | Color: yellowish, bright |
| | Consistency: mucous |
| NA + Mn | Shape: circular |
| | Edges: entire |
| | Elevation: raised |
| | Color: pale yellow, bright |
| | Consistency: mucous |

*B. licheniformis* V9T14 produced biosurfactants when grown on LB broth. The ability of lowering surface tension was verified using a du Nouy platinum ring digital Tensiometer. Bacteria grown on MSM glucose showed the beginning of biosurfactant production after 24 h. When grown on LB broth, they showed a production peak after 24 h at the end of the log phase (FIG. 1).

*Bacillus licheniformis* V9T14 was able to grow in the presence of 5% NaCl and biosurfactant production was not affected by the presence of the halogen, reaching a surface tension of 36 mN/m after 24 h. Bacterial growth at 10% NaCl was highly slackened and biosurfactant production was inhibited.

Figure 2:
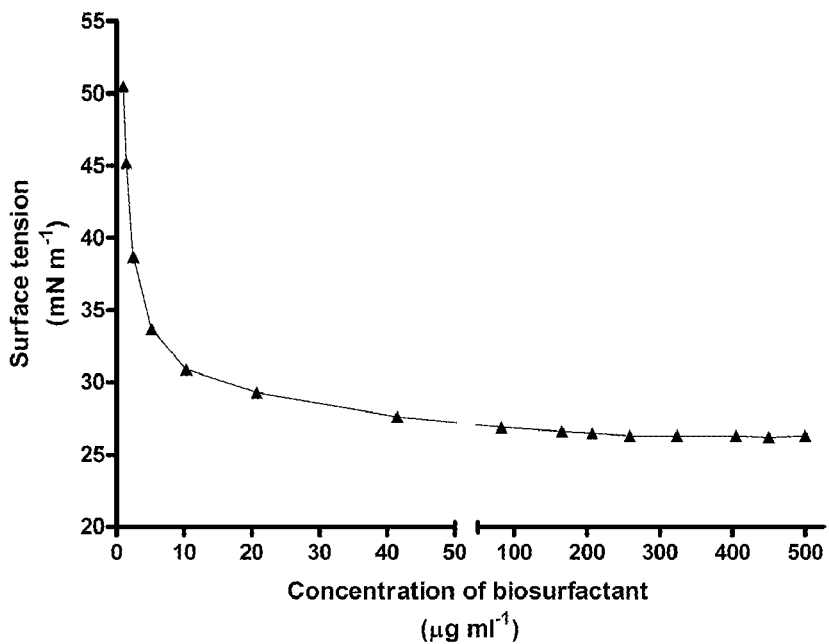
FIG. 2. A plot of surface tension as a function of concentration of V9T14 biosurfactant after extraction. Standard deviation was ranging between ±0.3 mN/m.

Biosurfactant obtained by solvent extraction appeared as amber-coloured resinous residue, probably due to the presence of small quantity of residual water in the extract. After few days at room temperature with low humidity level, it dried and it was possible to obtain a powder by scratching them with a spatula. The biosurfactant had a bad odour. V9T14 solution at 500 µg mL$^{-1}$ decreased water surface tension from 68.8 to 26.3 mN/m. Serial dilutions of V9T14 biosurfactant showed a constant surface tension value of 26 mN/m until concentration of 50 µg mL$^{-1}$ (FIG. 2). Then the values slowly increased to ranges between 27 and 30 mN/m until the concentration of 10 µg mL$^{-1}$. The CMC was calculated as the intercept of two straight lines extrapolated from the concentration-dependent and concentration independent sections of a curve plotted between biosurfactant concentration and surface tension values. The calculated CMC of V9T14 biosurfactant was 6.7 µg mL$^{-1}$.

FT-IR Spectroscopic Analysis

Figure 9:
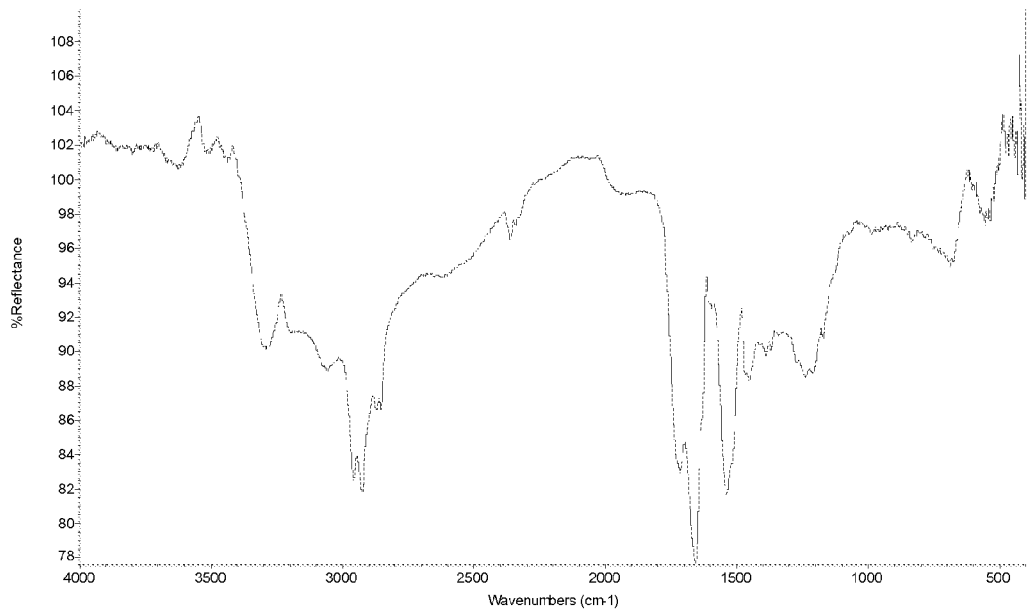
FIG. 9. FT-IR spectrum of V9T14.

The FT-IR spectrum of V9T14 in KBr (FIG. 9) showed strong absorption bands indicating the presence of peptides at 3300 cm$^{-1}$ resulting from N—H stretching mode at 1655 cm$^{-1}$ resulting from the stretching mode of the CO—N bond and the 1535 cm$^{-1}$ resulting from the deformation mode of N—H bond combined with C—N stretching mode. These results suggest that V9T14 biosurfactant contains peptide like moieties. The bands at 2960 to 2860 and 1470 to 1370 cm$^{-1}$ resulting from the C—H stretching mode reflect the presence of an aliphatic chain (—CH$_2$—, —CH$_3$). The absorption region at 1740-1680 cm$^{-1}$ was due to lactone carbonyl absorption.

MS and MS$^n$ Analysis

Figure 10:
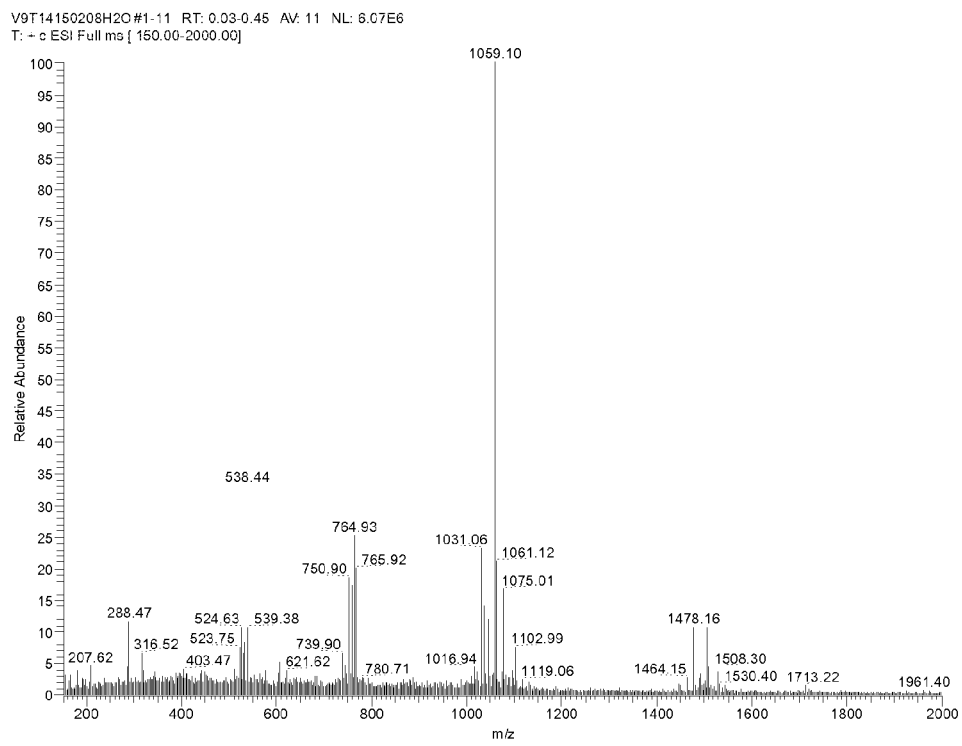
FIG. 10. ESI-MS positive full scan spectrum of crude lipopeptides extract.

Lipopeptides produced by V9T14 were firstly characterized through ESI-MS positive full scan mode spectra (FIG. 10). Two clusters of peaks with 14 or 28 Da difference in their molecular weight are present, revealing two sets of homologue molecules.

Figure 11:
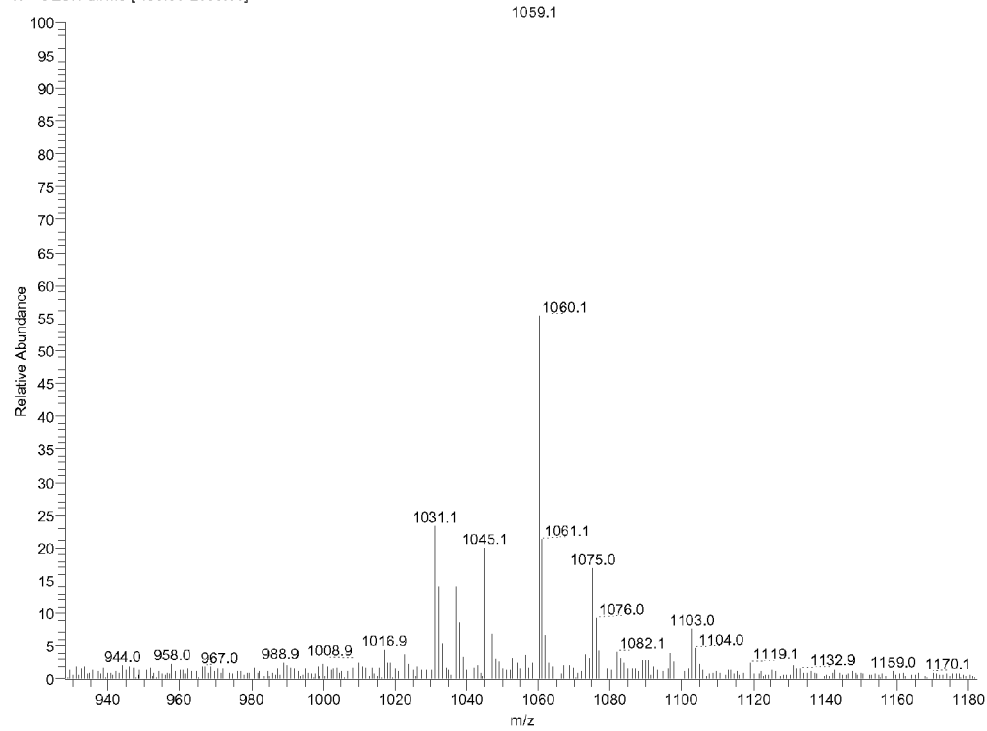
FIG. 11. ESI-MS positive full scan spectrum of crude lipopeptides extract, surfactin family.

The first set evidence three main peaks at m/z 1058.7, m/z 1044.7 and m/z 1030.7 that correspond to the sodiated molecules m/z M+Na]$^+$ of surfactin-molecules (FIG. 11). Besides, negative full scan mode spectra shows with three main peaks at 1034.5 m/z, 1020.5 m/z and 1006.5 m/z that correspond to the quasimolecular ions M−H]$^-$. Therefore, the molecular weight of the three molecules is respectively m/z 1036, 1022 and 1008. The three peaks differ of 14 Da, suggesting a difference in the carbon chain length (—CH$_2$—).

Figure 12:
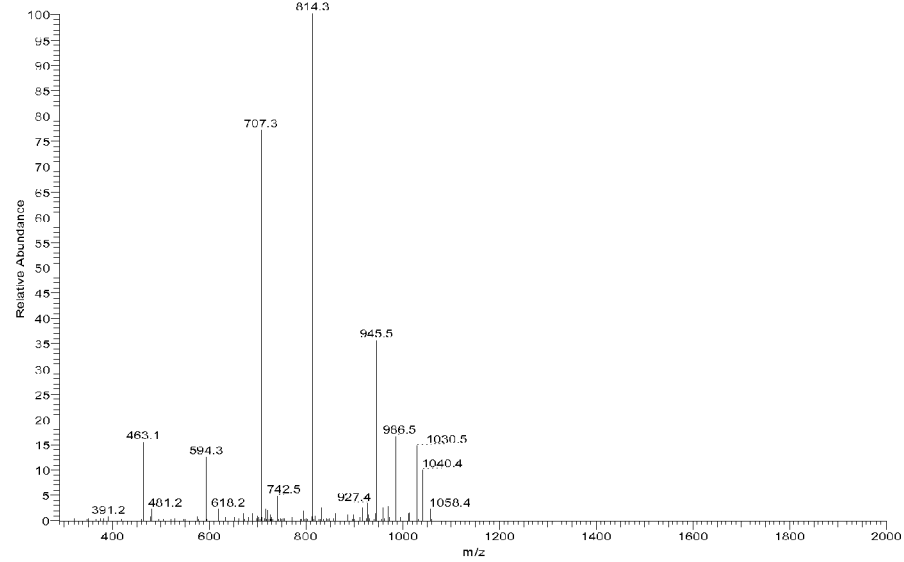
FIG. 12. ESI-MS/MS spectrum of the precursor ion m/z 1058.7.
Figure 13:
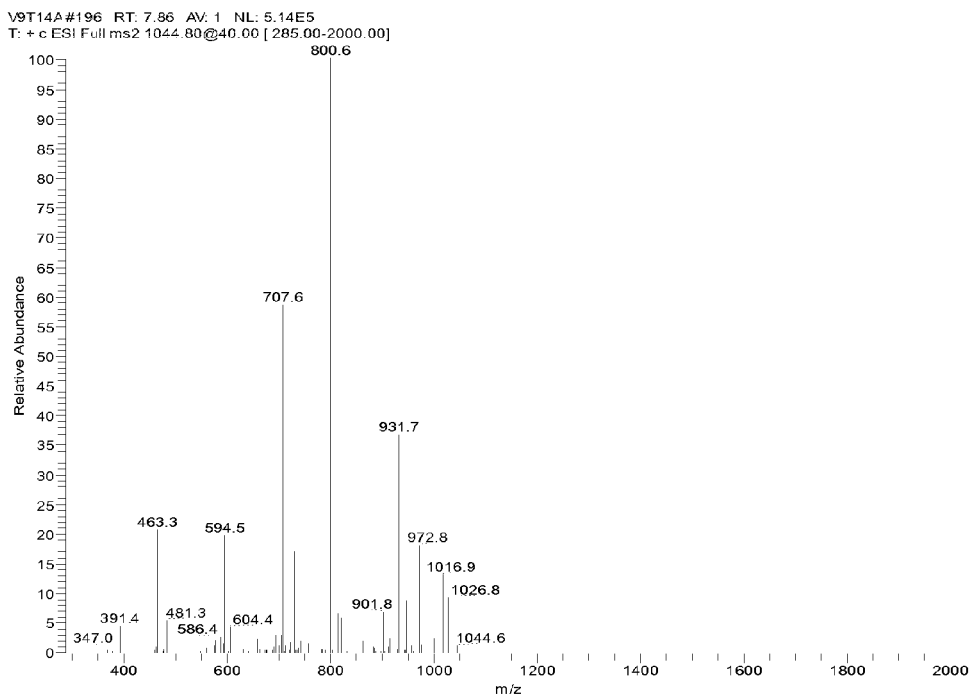
FIG. 13. ESI-MS/MS spectrum of the precursor ion m/z 1044.8.
Figure 14:
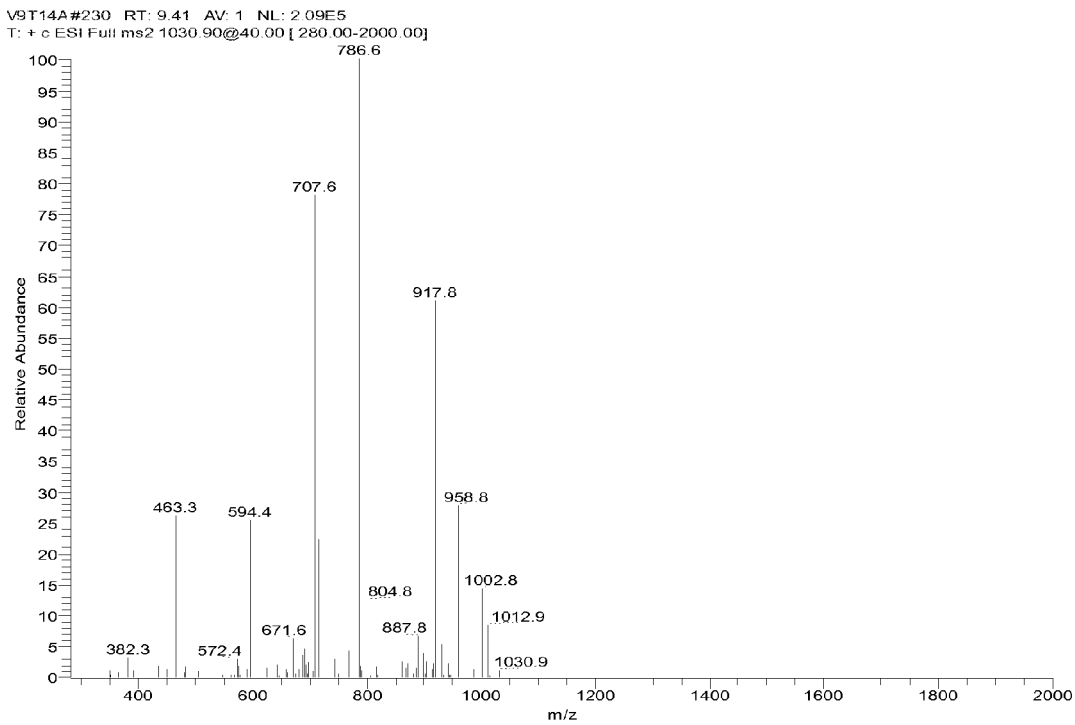
FIG. 14. ESI-MS/MS spectrum of the precursor ion m/z 1030.9.

The m/z 1058.7, 1044.7 and 1030.7 were used as precursor ion for further ESI-MS/MS analysis respectively (FIGS. 12, 13 and 14). The results showed that the appearance of product ions of these precursor ions had regularities.

Product ions of the precursor ion at m/z M+Na]$^-$ 1058.7 where found at m/z 1040.4, 945.5, 832.5, 814.3, 618.2, 707.3, 594.3, 481.2, 463.3 (FIG. 12). Ion at m/z 1040.4 corresponded to losses of water (−18 Da) from m/z M+Na]$^+$ 1058.6. The other product ions where identified as two series deriving from the initially opening of the lactone ring, one containing the fatty acid chain (m/z 945.5, 832.5, 814.3, 618.2) and the other one only relative to the peptidic portion (m/z 707.3, 594.3, 481.2, 463.3). Ions at m/z 945.5 corresponded to the loss of Leu (−113 Da) and at m/z 832.5 corresponded to the loss of Leu (−113 Da) from 945.5 m/z, while ion at m/z 814.3 corresponded to the loss of Leu-Leu-H$_2$O (−244 Da) from m/z 1058.6 and ion at m/z 618 m/z corresponded to the loss of Asp-Val- (−214 Da) from m/z 832. Product ion at m/z 707.3 correspond to the loss of C$_{15}$ β-hydroxyl fatty acid chain-Glu (−352 Da) from m/z M+Na]$^+$ 1058.6, ion at m/z 594.3 correspond to the successively loss of 1 Leu (−113 Da), ion at m/z 481.2 to the loss of another Leu (−113 Da) and ion at m/z 463.3 to the loss of Leu-H$_2$0 (−131 Da).

Product ions of the precursor at m/z M+Na]$^+$ 1044.6 where found at m/z 1026.5, 931.4, 818.5, 800.3, 604.2, 707.3, 594.3, 481.2, 463.3 (FIG. 13). Ion at m/z 1026.5 corresponded to losses of water (−18 Da) from m/z M+Na]$^+$ 1044.6. Ions at m/z 931.5 corresponded to the loss of Leu (−113 Da) and at m/z 818.5 corresponded to the loss of Leu (−113 Da) from 931.5 m/z, while ion at m/z 800.3 corresponded to the loss of Leu-Leu-H$_2$O (−244 Da) from m/z 1044.6. Ion at m/z 604 m/z corresponded to the loss of Asp-Val- (−214 Da) from m/z 818. Product ion at m/z 707.3 correspond to the loss of C$_{10}$ β-hydroxyl fatty acid chain-Glu (−338 Da) from m/z M+Na]$^+$ 1044.6, m/z 594.3 correspond to the successively loss of 1 Leu (−113 Da), m/z 481.2 to the loss of another Leu (−113 Da) and m/z 463.3 to the loss of Leu-H$_2$0 (−131 Da).

Product ions of the precursor at m/z M+Na]$^+$ 1030.6 where found at m/z 1012.5, 917.4, 804.5, 786.3, 590.2, 707.3, 594.3, 481.2, 463.3 (FIG. 14). Ion at m/z 1012.5 corresponded to losses of water (−18 Da) from m/z M+Na]$^+$ 1030.6. Ions at m/z 917.5 corresponded to the loss of Leu (−113 Da) and at m/z 804.5 corresponded to the loss of Leu (−113 Da) from 917.5 m/z, while ion at m/z 786.3 corresponded to the loss of Leu-Leu-H$_2$O (−244 Da) from m/z 1044.6. Ion at m/z 590 m/z corresponded to the loss of Asp-Val- (−214 Da) from m/z 804.5. Product ion at m/z 707.3 correspond to the loss of C$_{10}$ β-hydroxyl fatty acid chain-Glu (−338 Da) from m/z M+Na]$^+$ 1044.6, m/z 594.3 correspond to the successively loss of 1 Leu (−113 Da), m/z 481.2 to the loss of another Leu (−113 Da) and m/z 463.3 to the loss of Leu-H$_2$0 (−131 Da).

The product ions series containing the fatty acid portion of the precursor ions m/z 1058.7, 1044.7 and 1030.7 differ for each molecule of 14 Da, confirming a —CH$_2$ of difference in the fatty acid chain. The product ions series belonging to the peptidic moiety is equal for all the three homologues. These data are in accordance with mass spectra of surfactin standard Sigma.

Figure 15:
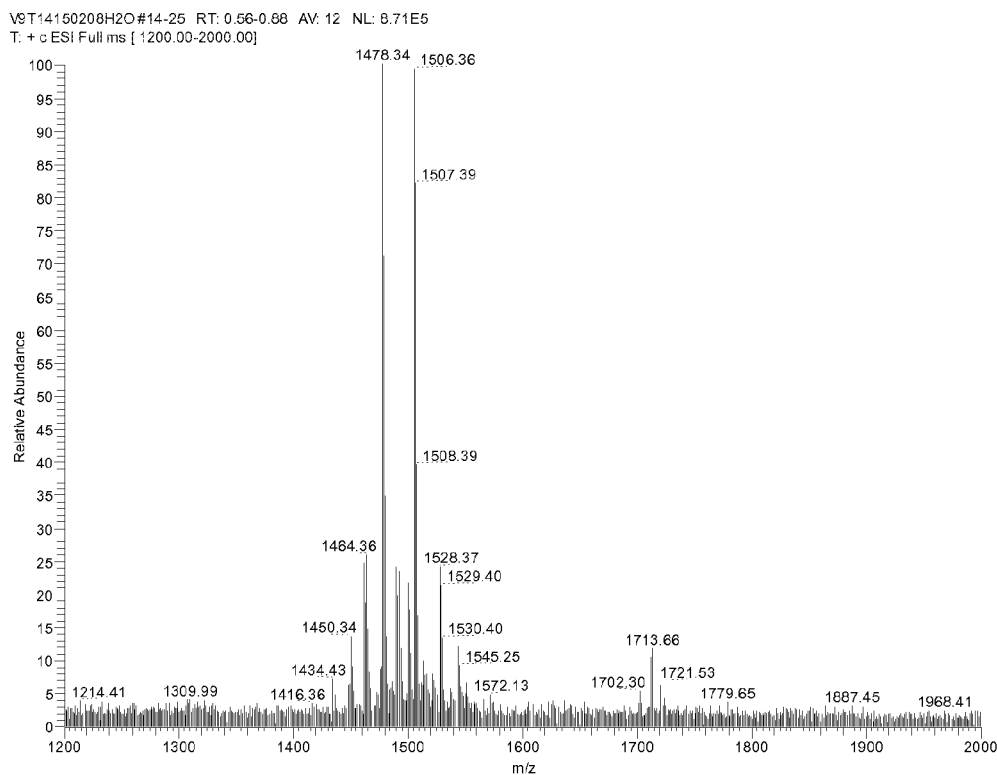
FIG. 15. ESI-MS positive full scan spectrum of crude lipopeptides extract, fengycin family.
Figure 16:
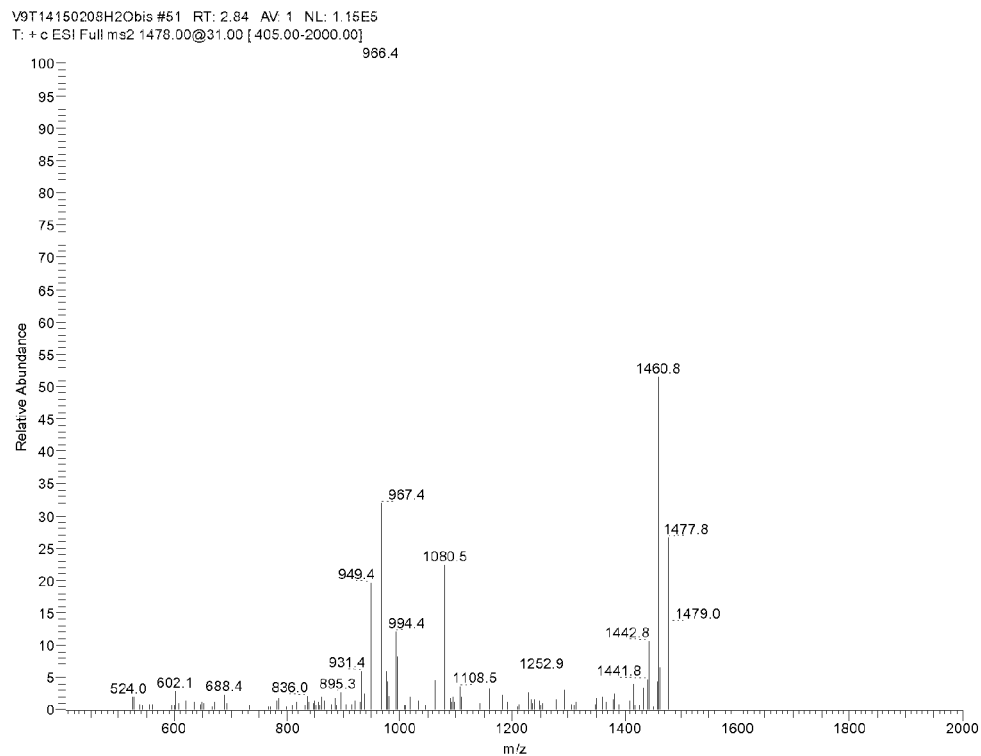
FIG. 16. ESI-MS/MS spectrum of the precursor ion m/z 1478.4.
Figure 17:
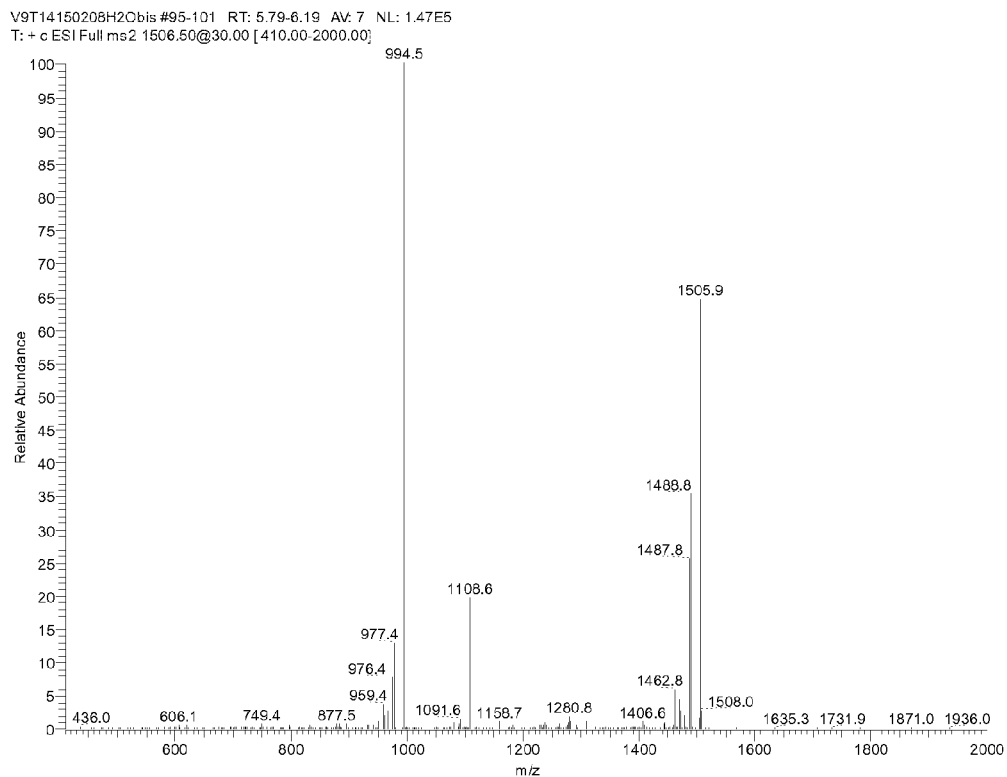
FIG. 17. ESI-MS/MS spectrum of the precursor ion m/z 1506.4.

The second set evidence two main peaks at m/z 1478.4 and m/z 1506.4 that correspond to the quasimolecular ions m/z M+H]$^+$ of fengycin molecules (FIG. 15). Besides, negative full scan mode spectra shows two main peaks at 1476.4 m/z, 1504.4 m/z that correspond to the quasimolecular ions M−H]$^-$. Therefore, the molecular weight of the two molecules is respectively m/z 1477, and 1505. The m/z 1478.4 and m/z 1506.4 were used as precursor ion for further ESI-MS/MS analysis respectively (FIG. 16, 17). The results showed the appearance of product ions of m/z 1080 and 966 as precursor ions of m/z 1478.4 (FIG. 16), and of m/z 1108 and 994 as precursor ions of m/z 1506.4 (FIG. 17). Product ions at m/z 1080 and 966 can be explained as neutral loses of fatty acid-Glu (−398 Da) and fatty acid-Glu-Orn (−512 Da) respectively from the N-terminus segment of fengycin-A. Product ions at m/z 1108 and 994 can be explained as neutral loses of fatty acid-Glu (−398 Da) and fatty acid-Glu-Orn (−512 Da) respectively from the N-terminus segment of fengycin-B. The two peaks differ of 28 Da, suggesting a difference in the aminoacidic composition of the peptide (Ala or Val). These results are in accordance with those observed by Wang et al. (2004); the precursor ions at m/z 1478.4 and m/z 1506.4 are fengycin A and fengycin B, respectively.

LC-MS Analysis

Figure 18:
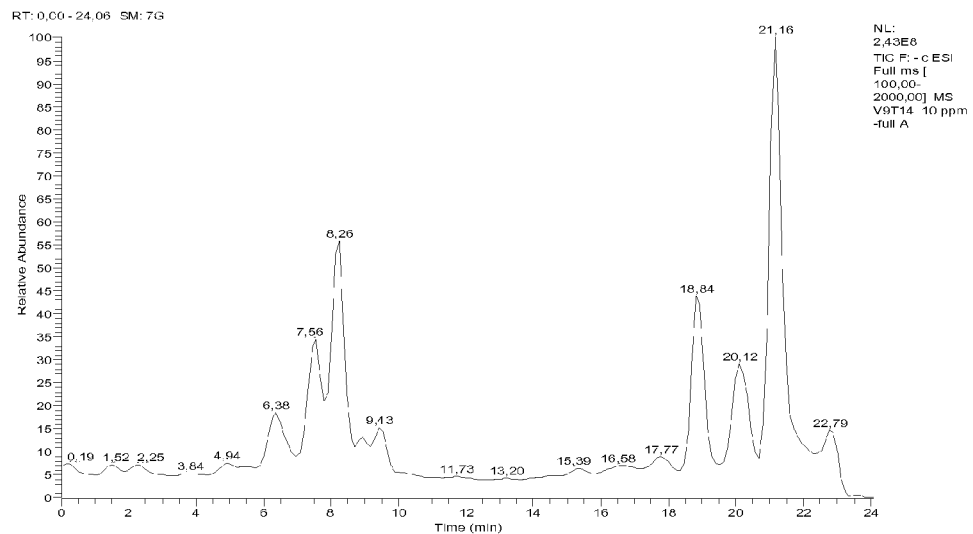
FIG. 18. HPLC-MS negative scan spectrum of biosurfactant extract V9T14.
Figure 19:
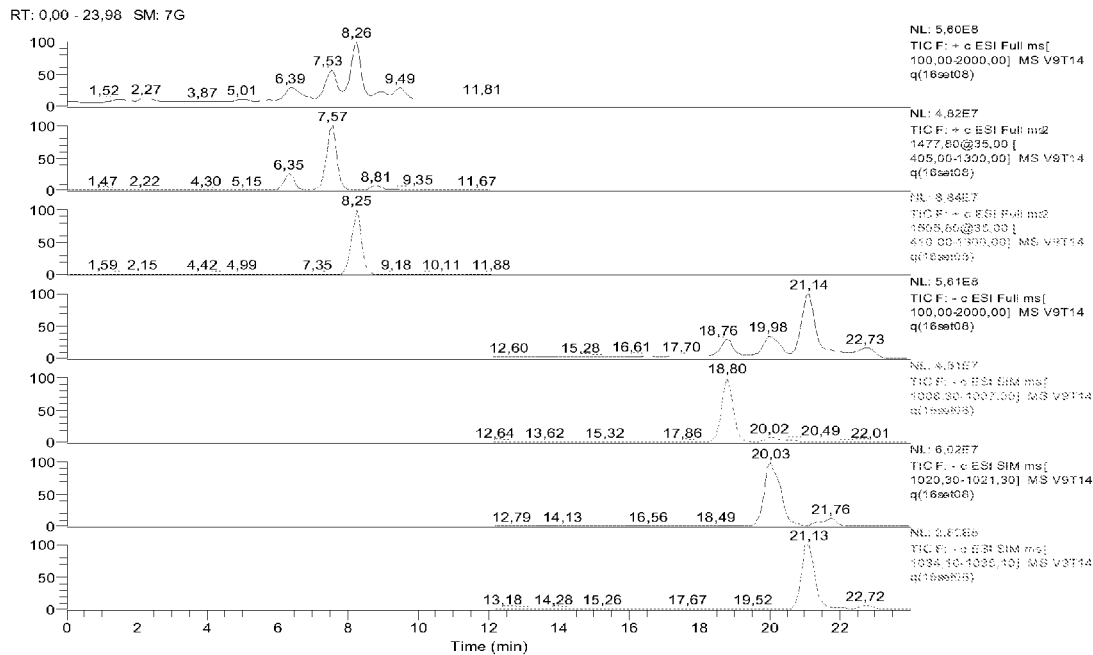
FIG. 19. HPLC-MS total ion chromatograms. Biosurfactant extract V9T14 fengycin and surfactin homologues are evidenced.

A mass chromatogram of biosurfactant V9T14 eluted from HPLC-ESI-MS analysis is presented in FIGS. 18 and 19. It can be observed, in the range of 3-10 min of retention time, the peaks corresponding to the main isoforms and homologues of fengycin molecules; in the range of 16-22 min three main peaks of homologues of surfactin molecules.

Characterizations of Lipopeptides Surfactin Group (Fraction B)

Fraction B eluted from silica gel chromatography showed, at TLC control, positive reaction with non specific reagent 4% potassium permanganate: the only spot visualized had the same Rf of surfactin standard (Sigma). The HPLC-ESI-MS confirmed the presence of mainly three homologues of surfactin at Rt 18.84 min (MW 1008), Rt 20.12 min (MW 1022), Rt 21.16 min (MW 1036), respectively surfactin C$_{13}$, surfactin C$_{14}$ and surfactin C$_{15}$. The HPLC-ESI-MS analysis of surfactin Sigma showed the same composition (same Rt and MW) but differences in the abundance of the homologues. If the areas of the peaks eluted between 16 and 22 min (FIG. 18) were summed to give the total surfactin peaks area for the surfactin-family of V9T14 biosurfactant, the relative content surfactin $C_{13}:C_{14}:C_{15}$ ratio in the range 15-29%:9-23%:54-69% is obtained (Table 5).

TABLE 5

| MW | surfactin-type | Rt (min) | Relative content % |
|---|---|---|---|
| 1008 | C-13 surfactin | 18.84 | 22.4 |
| 1022 | C-14 surfactin | 20.12 | 16.3 |
| 1036 | C-15 surfactin | 21.16 | 61.3 |

Characterizations of Lipopeptides Fengycin Group (Fraction D)

Fraction D eluted from silica gel chromatography showed, at TLC control, positive reaction with ninhydrin reactive. The ESI mass spectrum of fraction D revealed a cluster containing several molecules that were observed at M+H] m/z=1449.8, 1463.8, 1477.8, 1491.8, 1505.8 with the more intense at m/z 1477.8 and 1505.8. The m/z of these peaks showed high similarity to the fengycin homologues.

Figure 26:
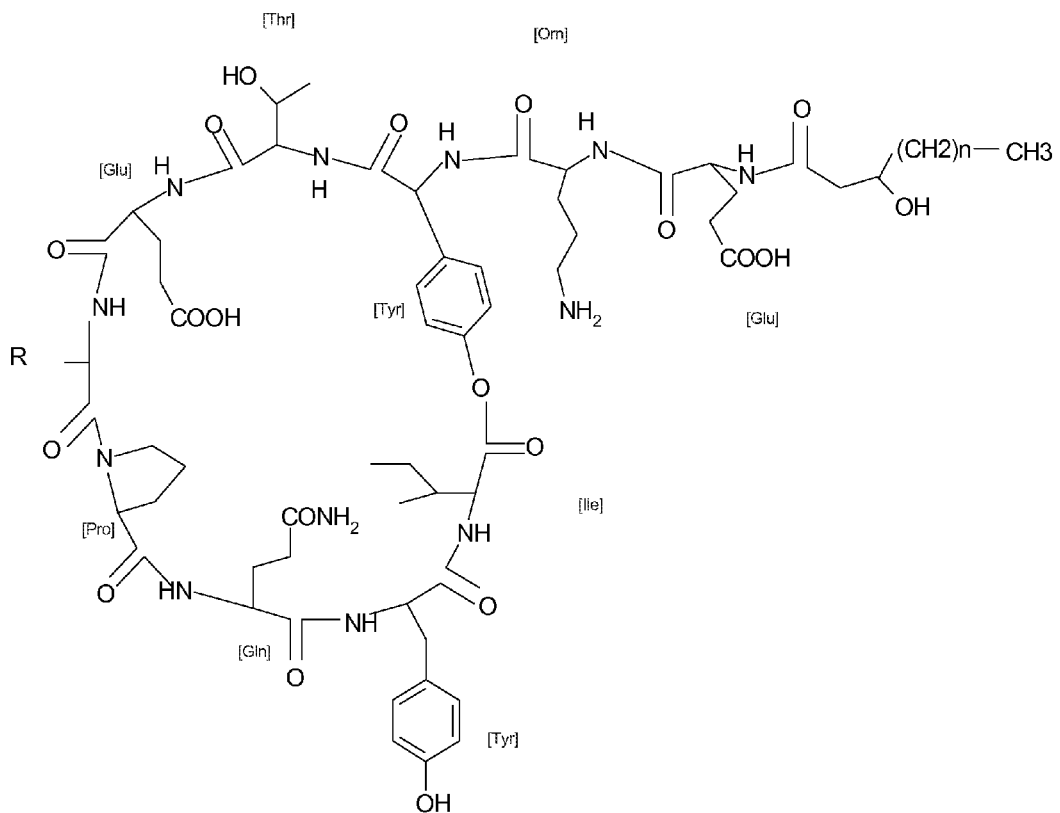
FIG. 26. The figure shows fengycin structure.

To confirm these structures, alkaline hydrolysis was done on the lipopeptides in fraction D. ESI-MS of the hydrolysate showed two main peaks at m/z 1495.8 and 1523.8, while the main peaks before the hydrolysis were at m/z 1477.8 and 1505.8, respectively. This mass gain of 18 Da could be assigned to hydrolysis of a lactone ring. The hydrolyzed peptides were further sequenced by ESI-MS/MS experiments: from the product ions obtained from the precursor at m/z 1523.8 the ring-opened peptide sequence was determined as Side chain-Glu-Orn-Tyr-Thr-Glu-Val-Pro-Gln-Tyr-Ile; from the product ions obtained from the precursor at m/z 1495.8 the ring-opened peptide sequence was determined as Side chain-Glu-Orn-Tyr-Thr-Glu-Al-Pro-Gln-Tyr-Ile. These sequence are in accordance with fengycin B and fengycin A, respectivey (FIG. 26).

To go deeply with the ions observed in ESI-MS spectrum of fraction D, each of these ions was selected as a precursor ion for further HPLC-ESI-MS/MS analysis. The results showed that the appearance of production of the precursor ions had regularities: product ions of m/z 1080 and 966 were found in MS/MS spectra of precursor ions of m/z 1435.8, 1449.8, 1463.8, 1477.8, as well as fengycin A. Product ions of m/z 1108 and 994 were found in MS/MS spectra of precursor ions of m/z 1463.8, 1477.8, 1491.8, 1505.8 as well as fengycin B.

The above results could allow concluding that lipopeptide biosurfactant in fraction D was composed of two families of molecules belonging to fengycin A and fengycin B group as reported in Table 6.

TABLE 6

| MW | fengycin-type | Rt (min) | Relative content % |
|---|---|---|---|
| 1435 | C-14 fengycin A | 3.80 | 0.9 |
| 1449 | C-15 fengycin A | 4.66 | 2.9 |
| 1463 | C-16 fengycin A | 6.66 | 3.3 |
| 1477 | C-17 fengycin A | 7.57 | 25.1 |
| 1463 | C-14 fengycin B | 5.91 | 0.7 |
| 1477 | C-15 fengycin B | 6.00 | 4.9 |
| 1491 | C-16 fengycin B | 7.21 | 7.2 |
| 1505 | C-17 fengycin B | 8.26 | 55.1 |

Effect of NaCl Concentration and pH

Figure 3:
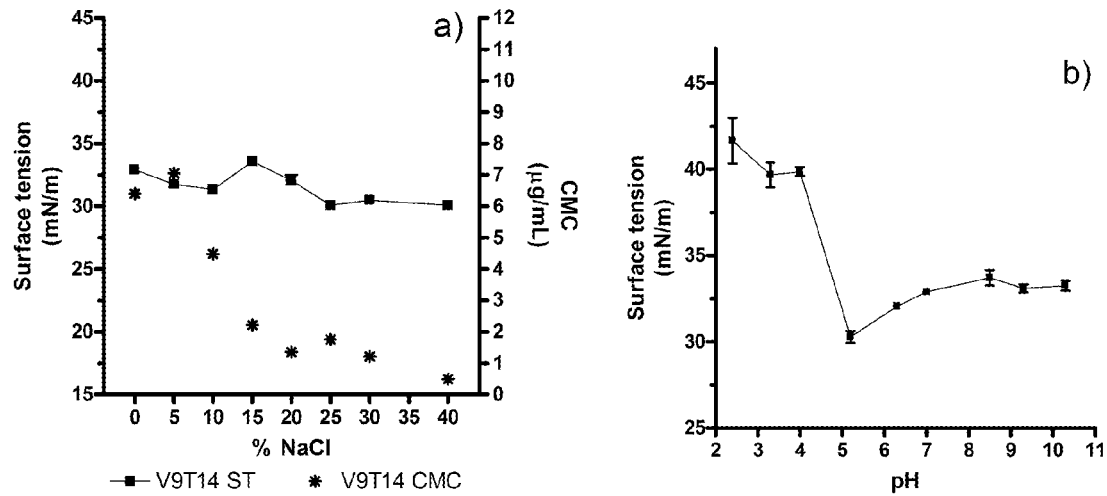
FIGS. 3a and 3b. Surface tension of extracted V9T14 biosurfactant as a function of NaCl concentration (3a) and pH (3b). For NaCl dependence (3a), biosurfactant was dissolved in water, and the final pH was adjusted to 7.0 with 1N NaOH. Different concentrations of halogen were dissolved in the solution. CMC was calculated as the intercept of two straight lines extrapolated from the concentration-dependent and concentration-independent sections of a curve plotted between biosurfactant concentration and surface tension values. For pH dependence (3b), pH was adjusted with 3N NaOH or 3N HCl and surface tension was measured. Surface tension of distilled water at pH 7.0 was 71.2 mN/m. Surface tension was measured in triplicate by a du Nouy ring tensiometer.

The V9T14 biosurfactant decreased the surface tension at high NaCl concentration up to saturation (FIG. 3.a). Initial surface tension of V9T14 biosurfactant solution was 33 mN/m, and remain almost stable for concentration up to 25% showing values ranging from 31 to 33 mN/m. Then a small decrease to 30 mN/m from 25% to saturation (more than 35%) was observed. CMC showed a small increase at 5% NaCl, from 6.4 µg/mL to 7 µg/mL, then drastically decrease to 0.5 µg/mL at NaCl saturation. The effect of various pH values on biosurfactants surface activity is shown in FIG. 3.b. V9T14 biosurfactant has a poor surface activity at pH from 2 to 4, decreasing from 71 mN/m to about 40 mN/m; while good surface activity was detected starting from pH 5 to 10 (30-33 mN/m), with maximum activity at pH 5 (30 mN/m).

Influence of Biosurfactants on Biofilm Formation by Different Bacterial Strains

Biofilm formation on CBD by bacterial strains was measured according to the procedure described by Harrison et al. (2006). The anti-adhesive effect of V9T14 biosurfactant was considered positive if, after 24 h of growth, there was a ≧1 $\log_{10}$ (90%) difference in the mean of CFU/peg compared to the growth control. The four strains tested, *E. coli* CFT073, *S. aureus* ATCC 29213, *P. aeruginosa* PA14 and the clinical *S. epidermidis* efficiently formed biofilms on the used media.

Figure 4:
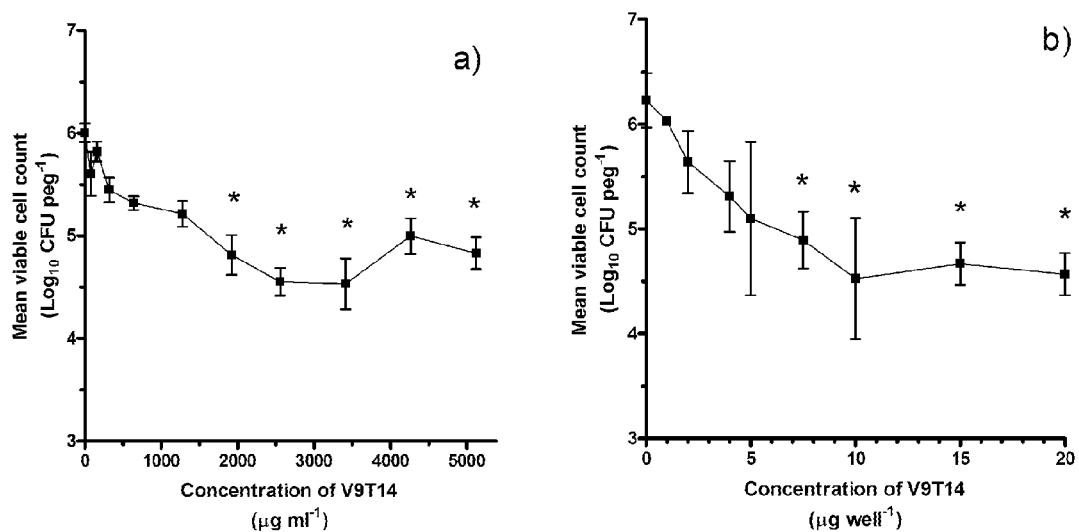
FIGS. 4a and 4b. The adhesion of *E. coli* CFT073 biofilm in the presence of different concentrations of V9T14 biosurfactant by precoating the Calgary Biofilm Device (CBD) pegs (4a) or by adding different amounts of V9T14 to each well of a 96-well plate (4b). * P<0.01
Figure 5:
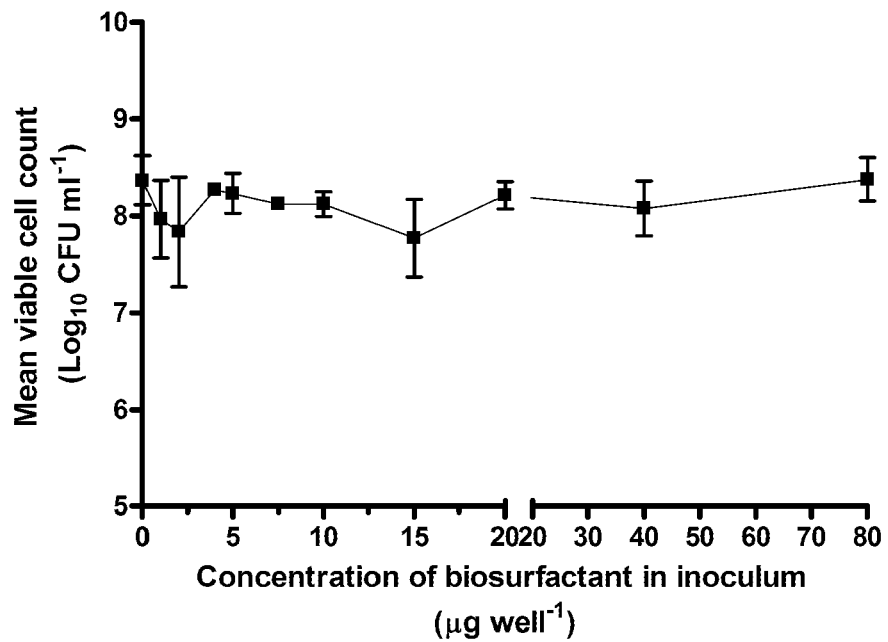
FIG. 5. Influence of V9T14 biosurfactant on planktonic *E. coli* CFT073 growth.

The increase of V9T14 biosurfactant concentration, promoted a decrease in *E. coli* CFT073 adherent viable cell count, to reach a maximal inhibition of 97% compared to the growth control with a precoating concentration of 2560 µg/mL (FIG. 4a) or by adding 10 µg/well (FIG. 4b) of biosurfactant with the inoculum. Statistical analysis of the biofilm viable cell count in the presence or absence of V9T14 showed a significant activity of the biosurfactant (p<0.0001).

Figure 6:
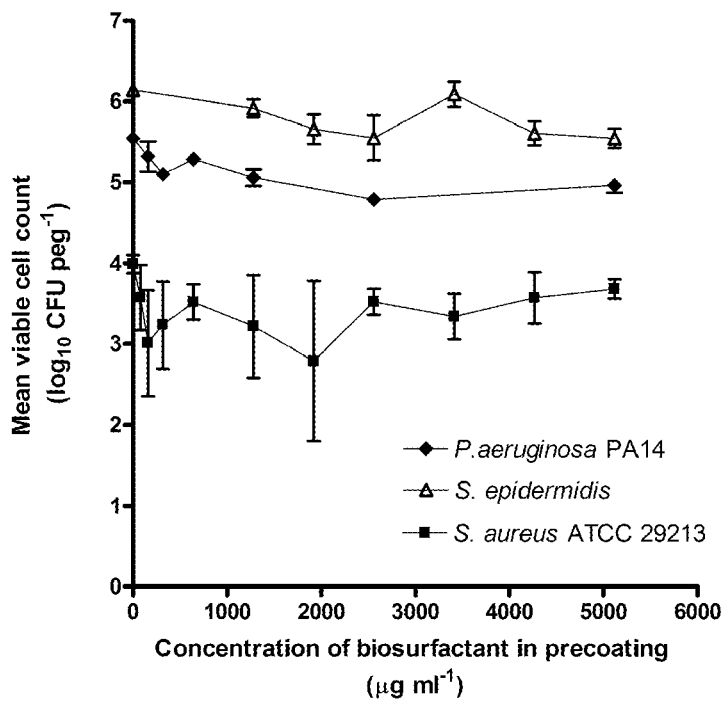
FIG. 6. Effect of V9T14 biosurfactant against microbial adhesion of different strains.

There was no apparent effect on planktonic survivability (FIG. 6) by the presence of V9T14 (p=0.46) biosurfactant, at every concentration tested.

V9T14 biosurfactant was not able to inhibit the adhesion of other microorganisms, in particular *S. aureus* ATCC 29213, *P. aeruginosa* PA14 and the isolate *S. epidermidis*. Viable cell count showed no difference in bacterial population of these microorganisms when V9T14 biosurfactant was present on the pegs or in the culture broth, even with high concentration of biosurfactant.

Figure 7:
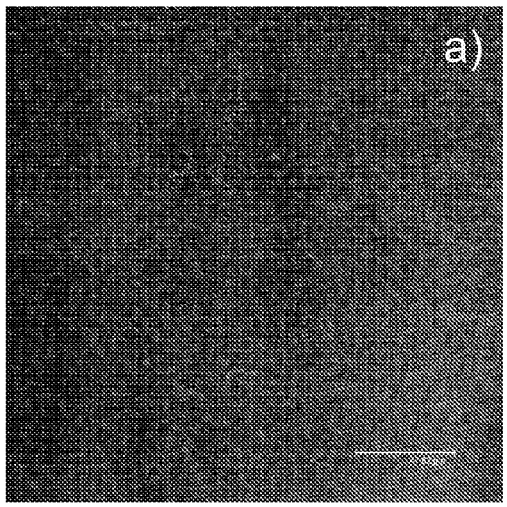
FIGS. 7a and 7b. Confocal Laser Scanning Microscopy analysis of Acridine Orange stained *E. coli* CFT073 biofilm formation growth in the presence of V9T14. Untreated control (7a) and inhibition of bacterial adhesion by V9T14 (7b) are shown. Bacteria were incubated in the Calgary Biofilm Device in LB broth with or without the biosurfactant and analysed for biofilm formation after 24 h using CLSM. Concentration of V9T14 biosurfactant was 10 μg/well.
Figure 7:
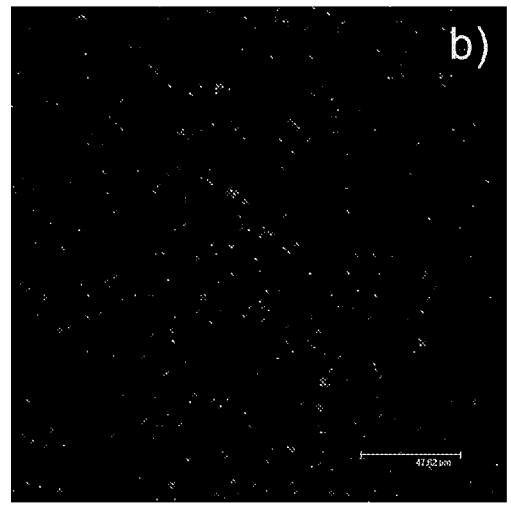

FIG. 7 presents CLSM images of *E. coli* CFT073 growth control (FIG. 7a) and adhesion in presence of V9T14 biosurfactant (FIG. 7b). *E. coli* CFT073 showed a dramatic decrease of adhesion when V9T14 biosurfactant was present on the peg or in culture broth.

Figure 27:
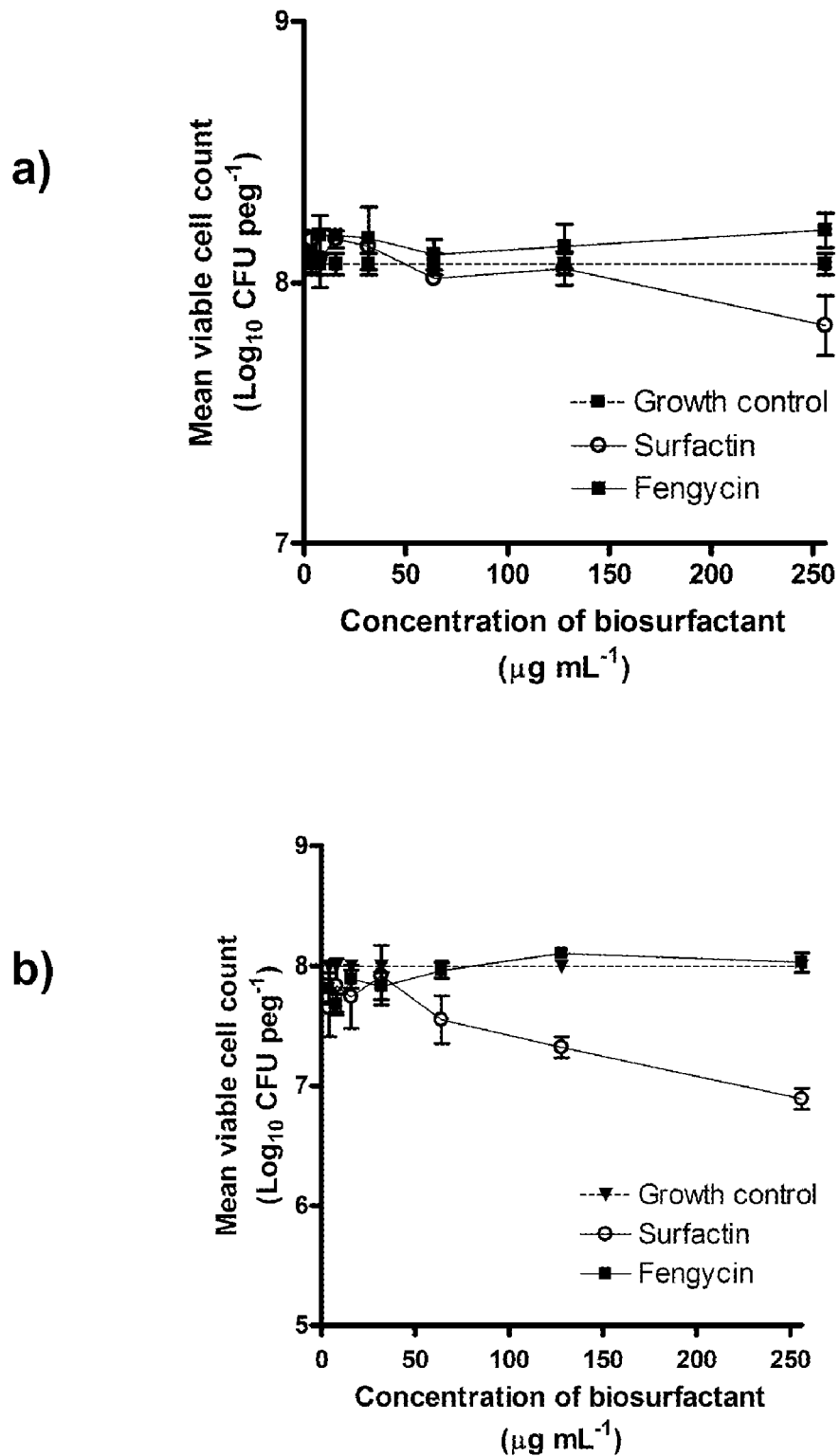
FIGS. 27a and 27b. Influence of V9T14 surfactin and fengycin fractions on planktonic *E. coli* CFT073 (27a) and *S. aureus* ATCC 29213 (27b) growth. The two fractions were dissolved in PBS and used in a concentration range from 4-256 µg/mL (27a and 27b).
Figure 28:
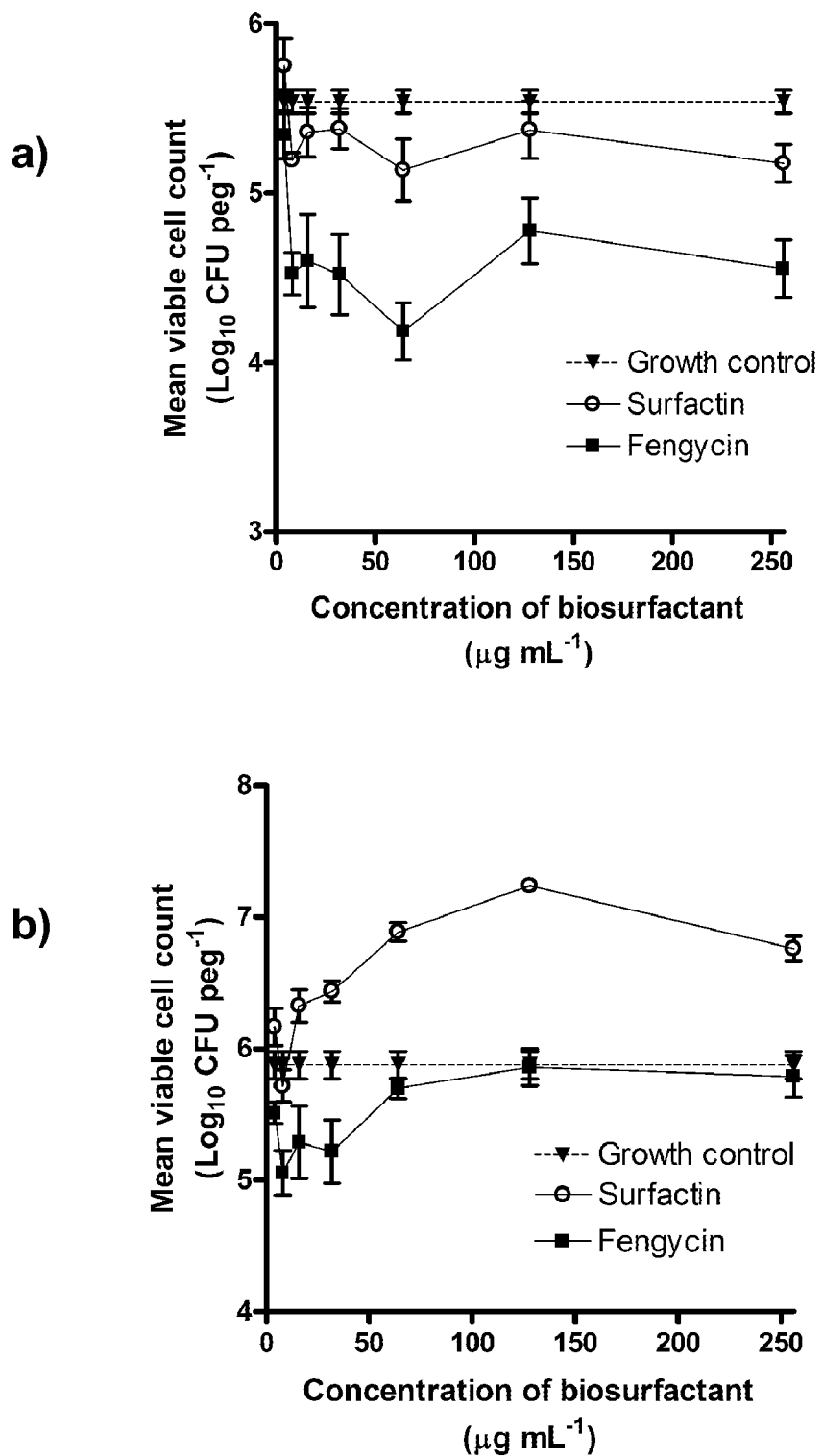
FIGS. 28a and 28b. Influence of V9T14 surfactin and fengycin fractions on biofilm *E. coli* CFT073 (28a) and *S. aureus* ATCC 29213 (28b) growth. The two fractions were dissolved in PBS and used in a concentration range from 4-256 µg/mL. Biofilm was grown at 37° C. for 24 h under shearing forces (28a and 28b).

Influence of Surfactin and Fengycin HPLC Purified Fractions on Biofilm Formation The two fractions of V9T14 biosurfactant, corresponding to surfactin molecules and fengycin molecules, obtained from HPLC were tested for biofilm inhibition to define which fraction was responsible for the anti-adhesive properties against the strain *E. coli* CFT073.

surfactin and fengycin showed no activity against planktonic *E. coli* CFT073 (FIG. 27a), while only surfactin showed activity against planktonic *S. aureus* ATCC 29213, resulting in almost 1 $\log_{10}$ inhibition at the concentration of 256 µg/mL (FIG. 27b).

fengycin was able to inhibit *E. coli* CFT073 biofilm adhesion (FIG. 28a) of about 90-95% (i.e. 1.4±0.2 $\log_{10}$ inhibition) starting from the concentration of 8 µg/mL up to 256 µg/mL. surfactin too affected the adhesion of *E. coli* CFT073 of about 60-70% (i.e. 0.4±0.1 log 10 inhibition) from the concentration of 8 µg/mL.

fengycin was able to inhibit S. aureus ATCC 29213 (FIG. 28b) of about 90% (i.e. 1 $\log_{10}$ inhibition) at concentration ranging from 4 to 32 µg/mL. surfactin, on the contrary, was not able to reduce the adhesion of S. aureus ATCC29213, but increases biofilm adhesion.

Influence of Combination of V9T14 Biosurfactant with Antibiotics on Planktonic and Biofilm forms of Different Bacterial Strains The killing of E. coli CFT073 biofilm and planktonic cultures was examined by ampicillin and piperacillin (penicillins), cefazolin and ceftriaxone (cephalosporins), ciprofloxacin (fluoroquinolone), tobramycin (aminoglycoside) and trimethoprim/sulfamethoxazol (dihydrofolate reductase inhibitor) alone and in association with V9T14 biosurfactant. MIC, $MBC_{99.99\%}$ and $MBEC_{99.9\%}$ of antibiotics and/or V9T14 were determined three times each as described in methods.

Figure 20:
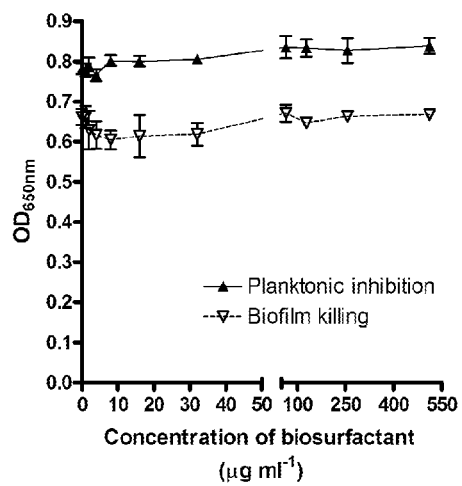
FIG. 20. Planktonic and biofilm susceptibility of *E. coli* CFT073 to V9T14 biosurfactant alone. Biofilm was grown into the Calgary Biofilm Device for 24 h at 37° C. under shearing forces, then was exposed to different concentrations of biosurfactant for 24 h.

A 24 h exposure to V9T14 biosurfactant alone was neither able to remove or eradicate an E. coli CFT073 biofilm nor to inhibit planktonic growth (FIG. 20) confirming that the inhibitory and the killing effect were absent at the concentration tested.

A 24 h exposure time of the antibiotics to define the concentration of each antimicrobial agent leading to complete growth inhibition was examined. The antibiotic susceptibility values of E. coli CFT073 under the various conditions are summarized in Table 7, wherein the tolerance values expressed as MIC, $MBC_{99.99\%}$ and $MBEC_{99.9\%}$ of antibiotics (Ab) and antibiotics plus biosurfactant (AbBs) against E. coli CFT073 for various antibiotics with or without biosurfactant are reported. MIC was defined as the lowest concentration of antibiotics presenting turbidity in a bacterial broth culture measured at $OD_{650\ nm}$, $MBC_{99.99\%}$ as the concentration needed to reduce planktonic viable cell count of 4 $\log_{10}$, $MBEC_{99.9\%}$ as the concentration to reduce biofilm viable cell count of 3 $\log_{10}$.

cfu/peg, while planktonic cultures were $3\times10^8$ cfu/mL. Data in FIGS. 21 and 22 demonstrate that the biosurfactant V9T14 increased the efficacy of several antibiotics.

Ampicillin (FIG. 22A) rapidly killed the vast majority of planktonic cultures at concentration up to 2 µg/mL. However, a portion ($10^2$ cfu/mL) of the planktonic population survived to ampicillin up to 16 µg/mL (FIG. 21a). For corresponding biofilm cultures (FIG. 22a), a reduction of 3 $\log_{10}$ was observed at 4 µg/mL, but a subpopulation of $10^3$ cfu/peg remain viable after 24 h exposure to the antibiotic alone. The association with V9T14 biosurfactant increases the killing of planktonic cells to complete eradication at 8 µg/mL. Also surviving biofilm population was reduced to $10^1$ cfu/peg using only 1 µg/mL of ampicillin, enhancing the effect of the antibiotic by 4 $\log_{10}$, and sessile forms were eradicated at 8 µg/mL. $MBC_{99.99\%}$ was not modified by the presence of V9T14 biosurfactant (Table 5) although the killing efficacy was further increased by 2 $\log_{10}$. $MBEC_{99.9\%}$ value was reduced from 4 to 0.5-1 µg/mL, and the co-administration of ampicillin and V9T14 biosurfactant increased the biofilm removal compared to the antibiotic alone. The association of ampicillin and biosurfactant thus significantly promotes reduction of planktonic and biofilm viable cell numbers.

Cefazolin (FIG. 22B) showed a concentration dependent killing curve for planktonic forms, killing more than 4 $\log_{10}$ cfu/mL at 16 µg/mL of antibiotic (FIG. 21b). Biofilm was reduced about 2.2 $\log_{10}$, but even at the highest concentration tested was not sufficient to reach an $MBEC_{99.9\%}$ value (FIG. 22b). The presence of V9T14 biosurfactant enhanced the effect against both planktonic and biofilm populations. $MBC_{99.99\%}$ was reduced from 16 to 8 µg/mL and the maximum killing effect observed was increased from 6.9 $\log_{10}$ at 32 µg/mL of cefazolin to 8.4 $\log_{10}$ when biosurfactant was present in a solution of cefazolin at the same concentration, leading to complete eradication of planktonic forms. $MBEC_{99.9\%}$ was decreased from more than 32 to 8 µg/mL.

TABLE 7

| Antibiotics | Ab MIC* | Ab MBC**$_{99.99\%}$ | AbBs MBC**$_{99.99\%}$ | Ab MBEC**$_{99.9\%}$ | AbBs MBEC**$_{99.9\%}$ |
|---|---|---|---|---|---|
| Ampicillin | 2-4 | 1-2 | 1-2 | 4 | 0.5-1 |
| Cefazolin | 1-2 | 16 | 8 | >32 | 8 |
| Cefriaxone | 1-2 | 0.5-1 | 0.5-1 | 1-2 | 0.5-1 |
| Ciprofloxacin | 8-16 | 0.25-0.5 | 0.25-0.5 | >2 | 1 |
| Piperacillin | >32 | >32 | >32 | >32 | >32 |
| Tobramycin | 16-32 | 8-16 | 8-16 | 2-4 | 2-4 |
| Trimethoprim/ Sulfamethoxazol | 8-16 | 1 | 1 | 1 | 1 |

*MIC values of antibiotics alone, expressed as µg/mL.
**expressed as µg/mL.

Figure 21:
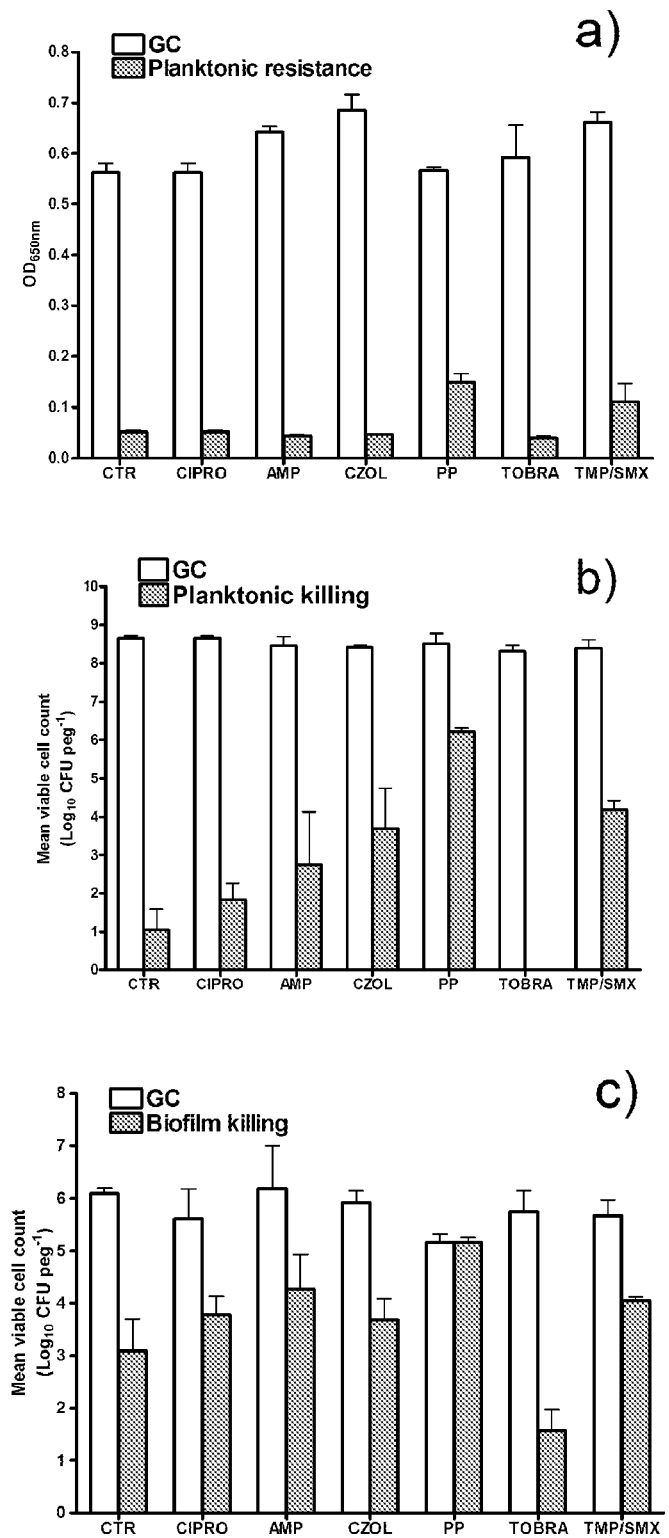
FIGS. 21a, 21b and 21c. Survival of planktonic and adherent microbial cells at the MIC value of antibiotics against *E. coli* CFT073 without the presence of V9T14 biosurfactant. Antibiotics tested were ceftriaxone (CTR at 1 μg/mL), ciprofloxacin (CIPRO at 1 μg/mL), ampicillin (AMP at 2 μg/mL), cefazolin (CZOL at 8 μg/mL), piperacillin (PP at 32 μg/mL), tobramycin (TOBRA at 16 μg/mL), trimethoprim/sulfamethoxazol (19:1) (TMP/SMX at 8 μg/mL). GC growth control. (21a) represents the inhibition of planktonic growth at MIC concentration. (21b) represents the killing effect of antibiotics against planktonic forms. (21c) represents the killing effect against mature biofilm.
Figure 22:
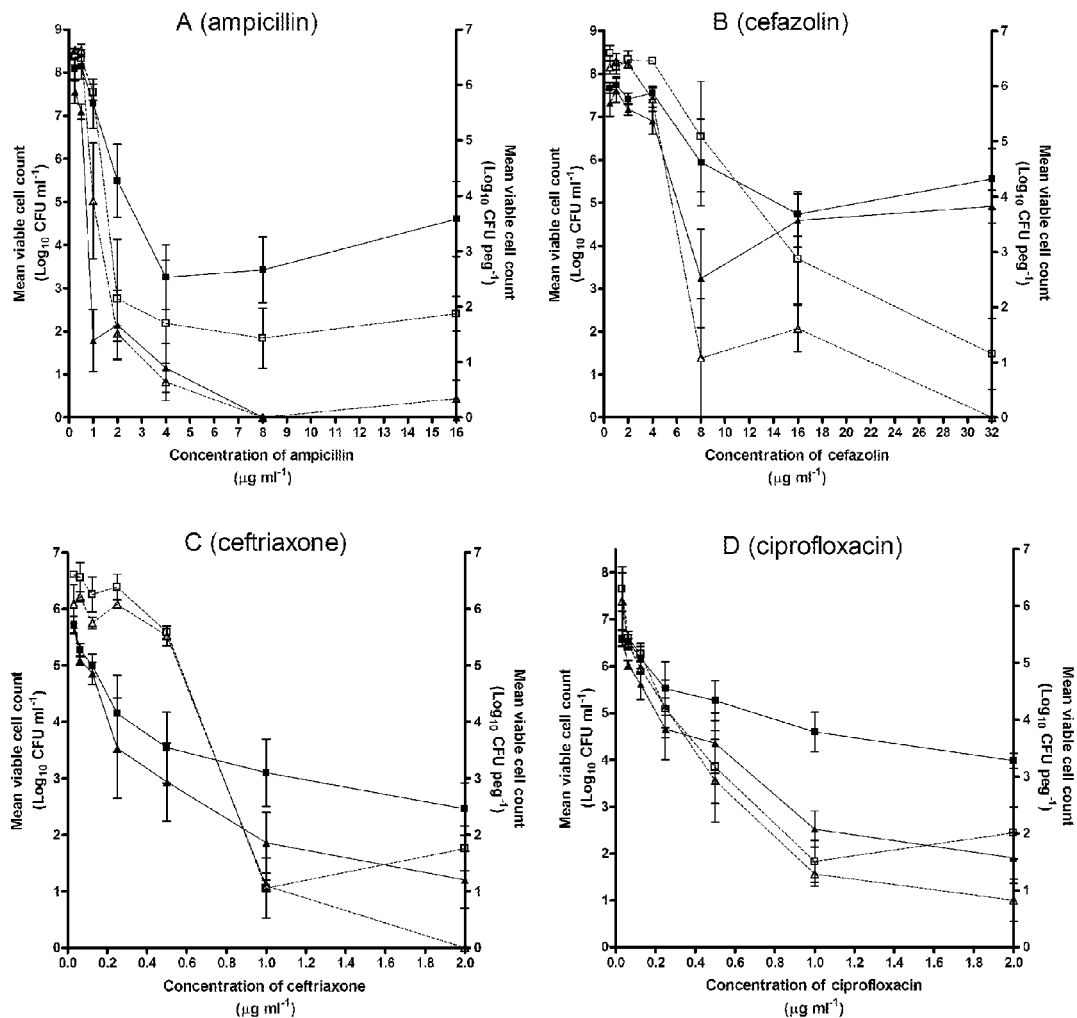
FIG. 22. Killing curves of *E. coli* CFT073 by antibiotics and antibiotics associated with 5 µg/mL V9T14 biosurfactant. Biofilms (solid line) and planktonic cultures (hatched line) were exposed to ampicillin (A), cefazolin (B), ceftriaxone (C) ciprofloxacin (D), piperacillin (E), tobramycin (F) and trimethoprim/sulfamethoxazol (19:1) (G) for 24 h in presence (triangle) or absence (square) of V9T14 biosurfactant. Data for planktonic and biofilm cultures are plotted in units of cfu per milliliter and cfu per peg in the MBEC™ device, respectively. Planktonic cells and biofilms were estimated by viable cell count. Each data point was calculated from a minimum of three replicates and a maximum of nine and the error bars indicate standard error.

FIG. 21 shows the effect of antibiotics on both planktonic and biofilm forms at the MIC value without biosurfactant. These data demonstrate the typical result of the antibiotics being very effective against the planktonic cells (FIGS. 21A and 21B) but considerably less effective against the biofilm cells (FIG. 21C).

A combination of V9T14 biosurfactant and antimicrobial agent was considered synergistic if, at 24 h exposure, there was a ≧1 $\log_{10}$ (90%) decrease in the mean of CFU/peg between the combination of the two agents and the antibiotic treatment on its own. FIG. 15 shows the mean viable cell count of planktonic and biofilm cultures as a function of concentration of antibiotics. In all experiments, biofilm growth control showed an approximate population of $8\times10^5$ The effect of ceftriaxone is shown in FIGS. 21c and 22c. Planktonic population was rapidly reduced by 3 $\log_{10}$ at 0.5 µg/mL and by 7 $\log_{10}$ at 1 µg/mL of antibiotic (FIG. 21c). Biofilm showed a dose dependent curve, killing 3 $\log_{10}$ of bacterial sessile population at 1 µg/mL of antibiotic (FIG. 22c). When ceftriaxone was associated with V9T14 biosurfactant, planktonic killing was modified only at the highest concentration tested, increasing the efficacy by only 1.7 $\log_{10}$ where no cultivable planktonic cells were detected by the presence of 2 µg/mL of antibiotic. Biofilm irradiation showed a similar trend for antibiotic alone, and only increased by 0.6 $\log_{10}$ in the range 0.25-0.5 µg/mL, and a further increase of 0.6 $\log_{10}$ for 2 µg/mL, reaching a final enhancement of 1.2 $\log_{10}$. $MBC_{99.99\%}$ was not modified, while $MBEC_{99.9\%}$ was decreased from 1-2 to 0.5-1 µg/mL.

Ciprofloxacin (FIG. 22D) showed the highest killing of planktonic forms at 1 μg/mL of antibiotic, with a 6.8 $\log_{10}$ reduction, with a concentration dependent curve up to 1 μg/mL, then as ciprofloxacin concentration increased, no further reduction was observed (FIG. 21d). Biofilm was reduced by 2.0-2.5 $\log_{10}$ at 1-2 μg/mL respectively (FIG. 22d). V9T14 biosurfactant did not significantly change the effect on planktonic forms up to 1 μg/mL, then it increase the killing ability by 1.4 $\log_{10}$ at 2 μg/mL. Biofilm removal was enhanced by 0.7 $\log_{10}$ in the range 0.25-0.5 μg/mL, and 1.7 $\log_{10}$ from 1 to 2 μg/mL of ciprofloxacin associated with biosurfactant. $MBC_{99.99\%}$ was not modified while $MBEC_{99.9\%}$ was decreased from more than 2 to 1 μg/mL.

Piperacillin (FIG. 22E—comparative example) was able to kill planktonic forms by 2.7 $\log_{10}$ at 4 μg/mL, then for further increases in concentration, no further effect on efficacy was observed (FIG. 21e). Similarly, the biofilm population was reduced by 1 $\log_{10}$ at 4 μg/mL with no increase of killing observed for further increase of antibiotic concentration (FIG. 22e). The presence of V9T14 biosurfactant showed no improvement either in planktonic or in biofilm population. $MBC_{99.99\%}$ and $MBEC_{99.9\%}$ values were not affected. The association of V9T14 biosurfactant and piperacillin was not able to satisfy our discrimination criterion for synergy identification.

The effect of tobramycin on E. coli CFT073 biofilm is shown in FIGS. 21f and 22f. A reduction of 1 $\log_{10}$ was observed in planktonic cultures up to 8 μg/mL of antibiotic, then, the efficacy rapidly increased to complete eradication of the planktonic population at 16 μg/mL (FIG. 21f). For corresponding biofilm cultures, a decrease of 4 $\log_{10}$ was observed, stabilizing the survival subpopulation of about $10^2$ cfu/mL at 8-16 μg/mL (FIG. 22f). Adding V9T14 biosurfactant to tobramycin solution, no increase of activity was noticed against planktonic cultures, while the increased efficacy of 1 $\log_{10}$ against sessile forms was observed at 16 μg/mL. $MBC_{99.99\%}$ and $MBEC_{99.9\%}$ values were not modified.

Trimethoprim/sulfmethoxazol (19:1) (FIG. 22G) reduced planktonic cells by 4.5-5 $\log_{10}$ at 2-4 μg/mL of antibiotics (FIG. 21g). Biofilm population was reduced by about 3 $\log_{10}$ at 1 μg/mL, then the reduction of population decreased a further 2 $\log_{10}$ up to 8 μg/mL (FIG. 22g). A surviving biofilm population of about $10^4$ cfu remains adherent to the peg of the CBD. The presence of V9T14 biosurfactant enhanced planktonic killing by 1.3 $\log_{10}$ at 16 μg/mL of antibiotics, while biofilm removal was enhanced by 1.5 $\log_{10}$ at 2-4 μg/mL. $MBC_{99.99\%}$ and $MBEC_{99.9\%}$ values were not modified.

Figure 23:
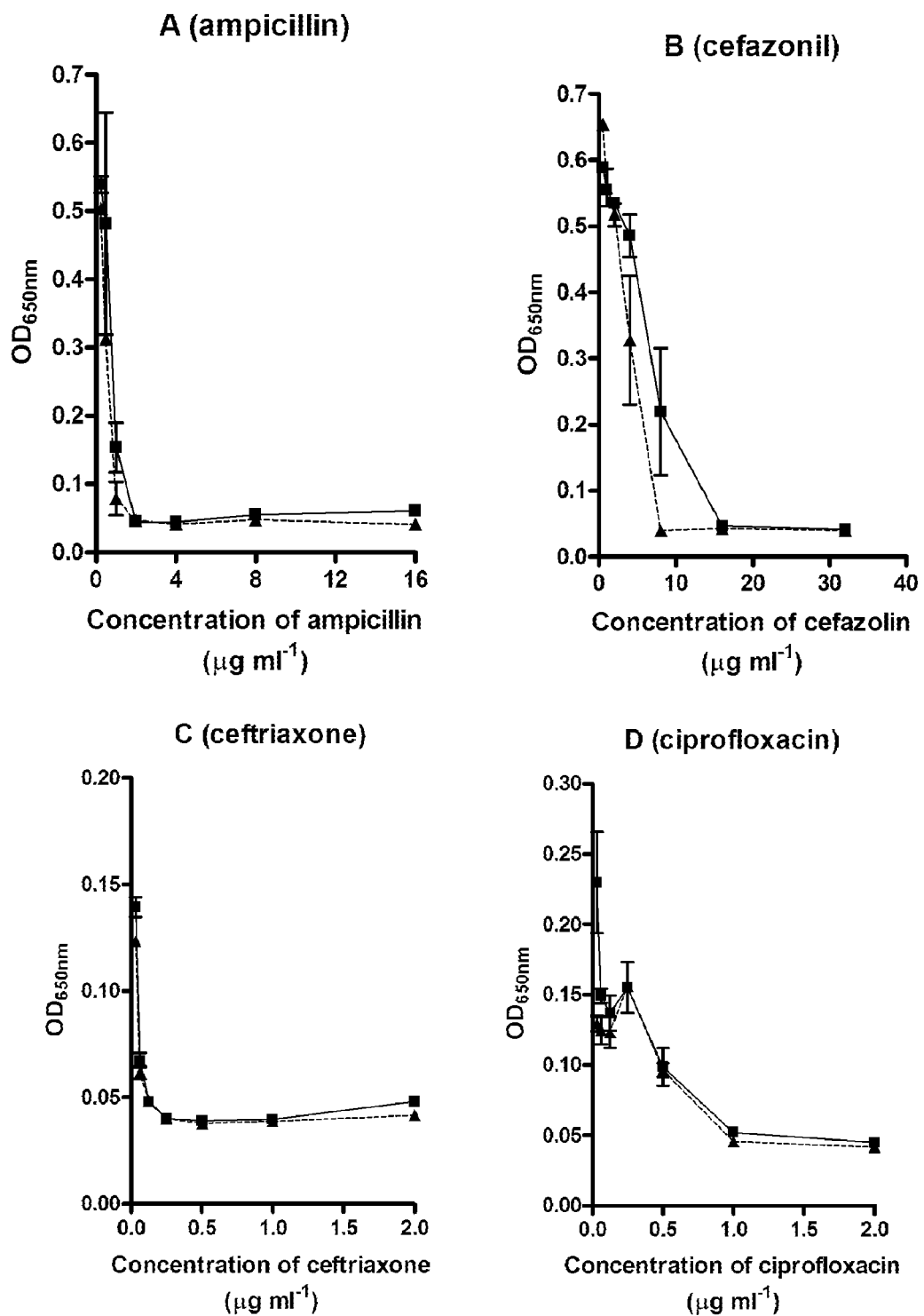
FIG. 23. Influence of V9T14 biosurfactant on antibiotic MIC values against *E. coli* CFT073 after 24 h of exposure evaluated by measuring the $OD_{650\ nm}$. OD optical density. Planktonic growth inhibition was evaluated for antibiotics alone (solid line) and antibiotics associated with 5 µg/mL of V9T14 biosurfactant (hatched line). Cultures were exposed to ampicillin (A), cefazolin (B), ceftriaxone (C), ciprofloxacin (D) piperacillin (E), tobramycin (F) and trimethoprim/sulfamethoxazol (19:1) (G) for 24 h. Each data point was calculated from a minimum of three replicates and the error bars indicate standard error.

The planktonic growth inhibition corresponding to each antibiotic was not improved by the presence of 5 μg/mL of V9T14 biosurfactant (FIG. 23), with the exception of cefazolin (FIG. 23B) for which MIC was decreased from 16 to 8 μg/mL and tobramycin (FIG. 23f), for which the association with 4 μg/mL of antibiotic was able to significantly inhibit the planktonic growth ($OD_{650}$ decreased from 0.31 to 0.18).

Figure 24:
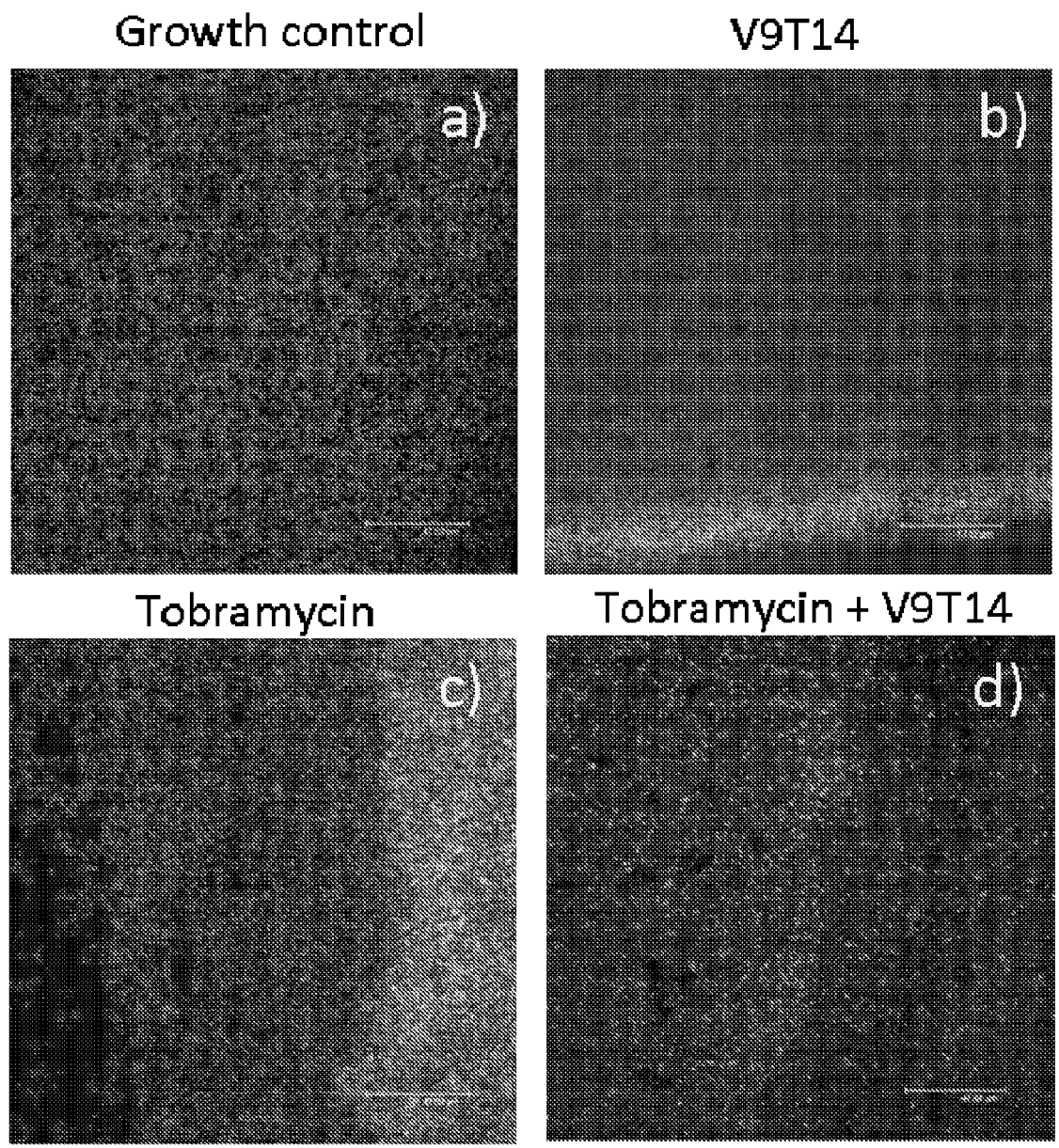
FIG. 24. CLSM image of Live/Dead stained *E. coli* CFT073 grown in the CBD. Images represent the *E. coli* growth biofilm (24a), treated with 5 µg/mL of V9T14 biosurfactant (24b), treated with 16 µg/mL of tobramycin (24c) and treated with 16 µg/mL of tobramicin in the presence of 5 µg/mL of V9T14 biosurfactant (24d).
Figure 25:
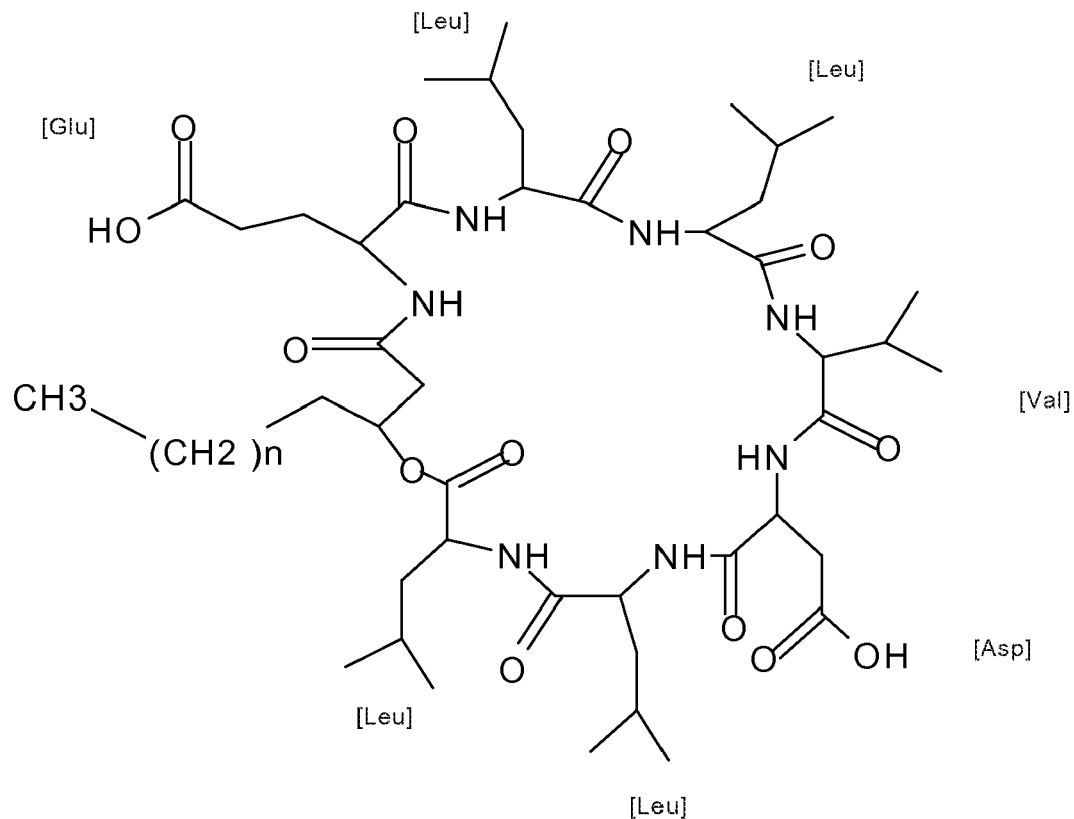
FIG. 25. The figure shows surfactin structure.

CLSM images show a mature E. coli CFT073 biofilm (FIG. 24a) after 48 h of growth at 37° C. When the mature biofilm was exposed to V9T14 biosurfactant for 24 h (FIG. 24b), no significant effect was observed. If the mature biofilm was exposed to 16 μg/mL of tobramycin (FIG. 24c), a significant killing of biofilm population was shown. When a combination of 5 μg/mL V9T14 biosurfactant and 16 μg/mL of tobramycin was present in broth culture (FIG. 24d), the mature biofilm reduction was further increased.

Influence of Combination of V9T14 Biosurfactant with biocides on Biofilm of E. coli CFT073

The adhesion of E. coli CFT073 to the peg was 6.3±0.4 $\log_{10}$ cfu/peg after 24 h, while 5.9±0.4 $\log_{10}$ cfu/peg when V9T14 biosurfactant alone was present, showing no evidence of biofilm removal activity.

Figure 29:
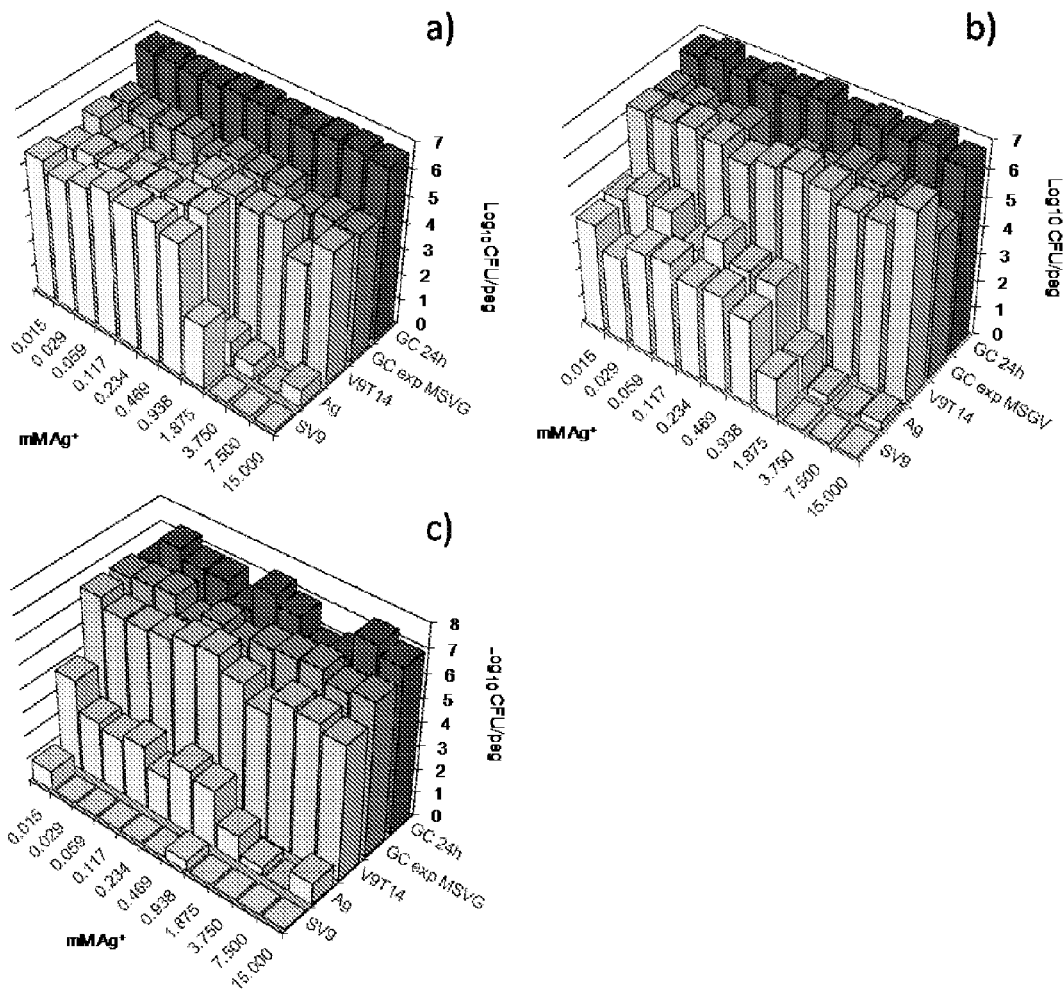
FIGS. 29a, 29b and 29c. Silver susceptibility after 2 h (29a), 8 h (29b) and 24 h (29c) exposure. *E. coli* biofilm was grown 24 h on the pegs of the CBD and then exposed to silver and silver+V9T14 (SV9) solutions. $AgNO_3$ dilutions were prepared in Minimal Salts Vitamins Glucose (MSVG). V9T14 biosurfactant was diluted in MSVG and added to a final concentration of 5 µg/mL.

After 2 h exposure (FIG. 29a), the presence of V9T14 enhanced the killing activity of silver by about 0.6 $\log_{10}$ at 3.750 mM. After 8 h (FIG. 29b) the increase was about 3.2 $\log_{10}$ (p=0.03) at the lowest concentration of silver tested (0.015 mM). After 24 h (FIG. 29.c), SV9 decreased biofilm viable cell count below the detection limit of the device (<10 cfu/peg). Using silver alone, the eradication of biofilm was observed at 7.5 mM, but when V9T14 biosurfactant was added, the eradication was at 0.029 mM of silver. At 0.015 mM, viable cell count was also reduced by 3.0 $\log_{10}$ compared to silver alone (p=0.0045).

To explain the observed activity after 24 h, the present inventors first hypothesized the formation of a coordination complex between the lipopeptide biosurfactant and the metal ion. To verify this hypothesis, SV9 solution was prepared 48 h before utilization and stored at room temperature in the dark to allow a possible reaction between the two compounds. Biofilms were then exposed to this solution for 2 and 4 h.

After 2 h (FIG. 30), results were comparable to those obtained with the freshly-prepared SV9 solution. The level of killing was higher than that observed in FIG. 28a, with an increase of about 1.1 $\log_{10}$ (p=0.03) at 1.875 mM compared to silver alone. The effect of silver alone at 15 and 7.5 mM was decreased compared to the freshly-prepared silver solution, but the presence of V9T14 biosurfactant restored its killing efficacy.

Figure 30:
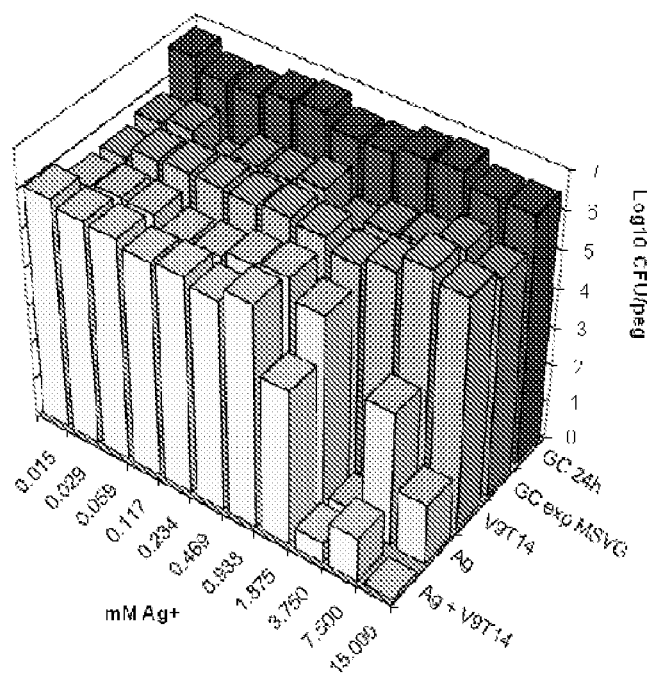
FIG. 30. Short time (2 h) exposure of a 24 h-old *E. coli* biofilm to pre-prepared silver and SV9 solutions (48 h before). V9T14 biosurfactant was diluted in MSVG, as well as $AgNO_3$. Final concentration of V9T14 added to each well was 5 µg/mL.

At 15 mM, freshly-prepared silver solution produced a precipitate, justifying the small lack of activity compared to 7.5 mM where the presence of precipitate was less (FIG. 29a). SV9 produced a precipitate as well. The precipitation of silver in the 48 h old SV9 was greater than that observed for the freshly-prepared solution. This increased precipitation leads to a decrease in free silver ions available for antibacterial activity, giving a possible explanation for the diminished activity of 48 h old SV9 compared to the freshly-prepared SV9 solution. Regardless, SV9 showed a lower level of precipitation compared to silver solution alone, possibly explaining the higher bactericidal activity of SV9 compared to silver solution (FIG. 30).

After 4 h of exposure, the killing efficacy of silver was increased of about 2.3 $\log_{10}$ (p=0.0007). Also in this case, as well as the 2 h exposure, no reduction of concentration needed to obtain complete eradication was observed.

Figure 31:
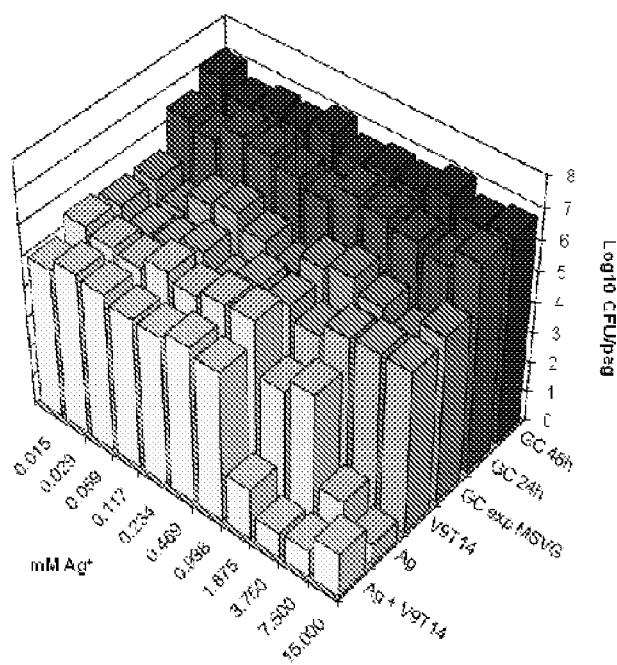
FIG. 31. Short time (2 h) exposure of a 48 h-old *E. coli* biofilm to freshly-prepared silver and SV9 solutions. V9T14 biosurfactant was diluted in MSVG, as well as $AgNO_3$. Final concentration of V9T14 added to each well was 5 µg/mL.
Figure 32:
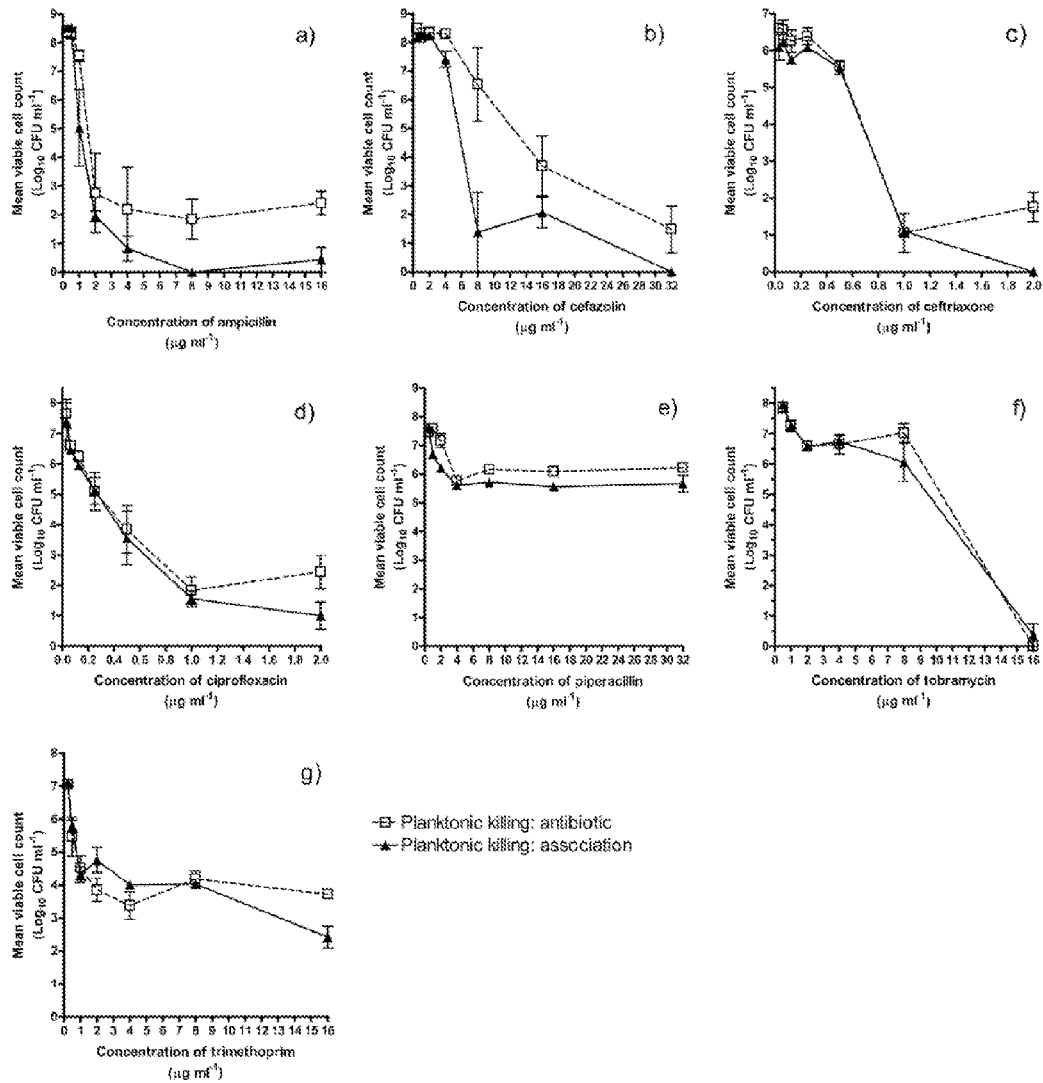
FIGS. 32 and 33. These figures correspond to FIG. 22, wherein the experimental data have been graphically reproduced in a clearer manner for a better understanding by the reader.
Figure 33:
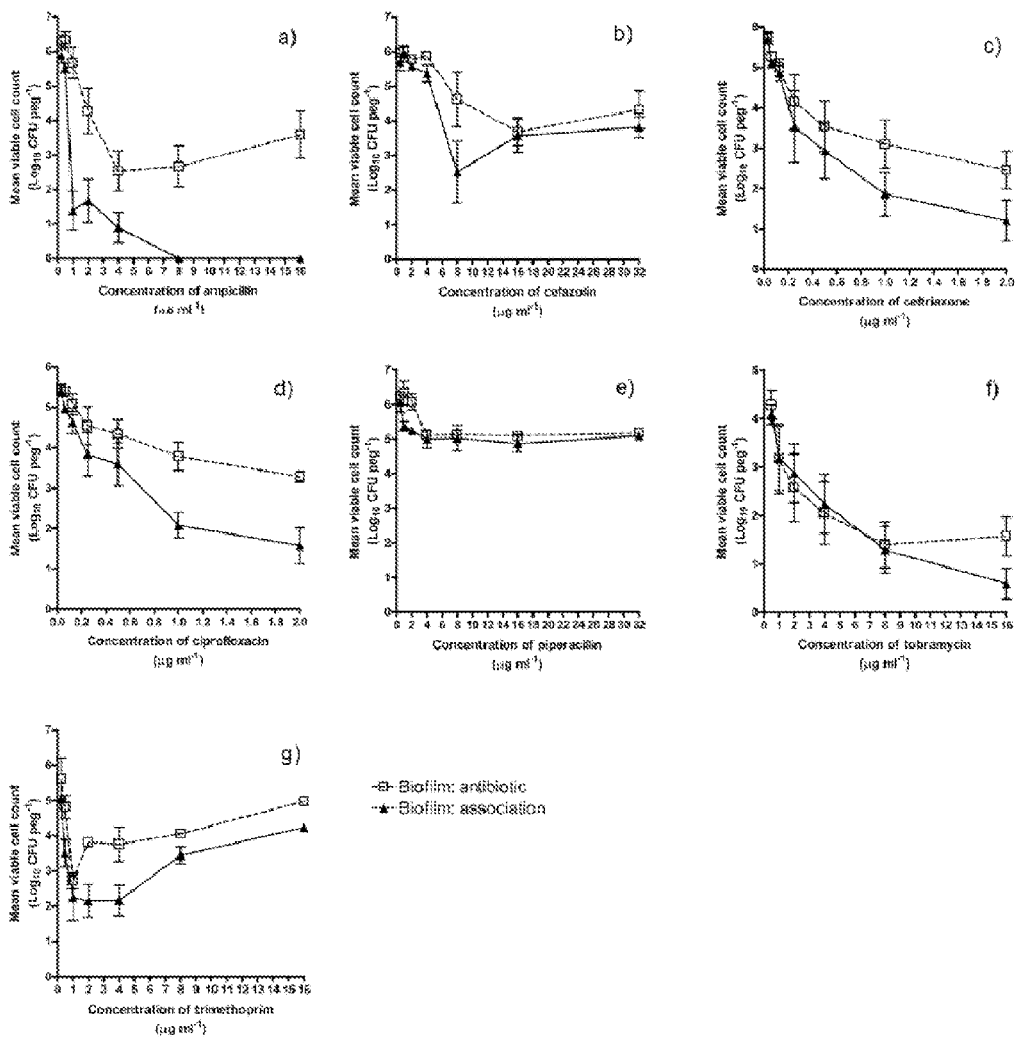

The present inventors also investigated the influence of biofilm age on SV9 activity. To define this, a 48 h-old biofilm was exposed for 2 and 4 h to silver and fresh SV9 solutions prepared just before use. At 2 h exposure (FIG. 31), results were comparable to those observed against the 24 h biofilm after the short time of exposure. The killing efficacy of SV9 was increased within the range from 2.3 (p=0.031) to 3.5 $\log_{10}$ (p=0.014) compared to silver solution alone. Similar results were observed for 4 h of exposure.

By definition, synergy occurs when two or more discrete agents act together to create an effect greater than the sum of the effects of the individual agents. In principle, synergy allows for a reduction in the quantity of agents used in combination yet might still allow for greater antimicrobial activity.

The association of silver ions with the biosurfactant led to an interesting increase of bactericidal activity after 24 h of exposure. The pre-formulation of SV9 solution can increase biofilm removal but it seems not to influence the concentration needed to eradicate the biofilm after a short exposure time (2 and 4 h). Moreover, results shows that biofilm age does not influence the activity of SV9 solution in biofilm removal.

Influence of Combination of V9T14 Biosurfactant with Silver on Planktonic forms of *E. coli* CFT073.

Figure 34:
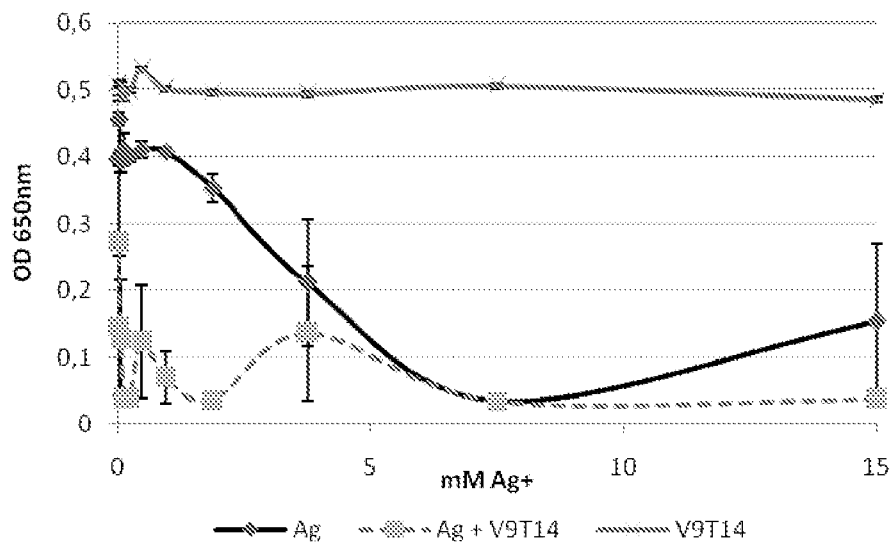
FIG. 34. Killing curve of planktonic *E. coli* CFT073 by silver, V9T14 biosurfactant, and silver associated with V9T14 biosurfactant after 24 h of exposure.

In the case of planktonic forms of *E. coli* CFT073, it was possible to observe an increase of activity of silver associated with V9T14 biosurfactant compared to silver alone (FIG. 34). It was also observed that V9T14 biosurfactant, at the concentration tested (5 µg/mL) was not able to affect the growth of planktonic *E. coli* CFT073. The complete inhibition of growth in presence of silver was observed for concentration of metal starting from 7.5 mM. When V9T14 biosurfactant was added to the silver solution, the concentration of metal able to inhibit bacterial growth was 64-fold less than that of silver alone.

Influence of Combination of V9T14 Biosurfactant with Different Biocides and Metals Uropathogenic *E. coli* CFT073

The V9T14 biosurfactant was combined with Polycide to control *E. coli* CFT073 biofilm population. The association with the biocide led to an increase in biofilm killing (FIG. 35).

The killing of Polycide with V9T14 was increased of about 0.9 $\log_{10}$, reducing the Polycide biofilm eradication concentration from 0.313% to 0.010%.

Entero Hemorrhagic *E. coli* O157:H7

Figure 35:
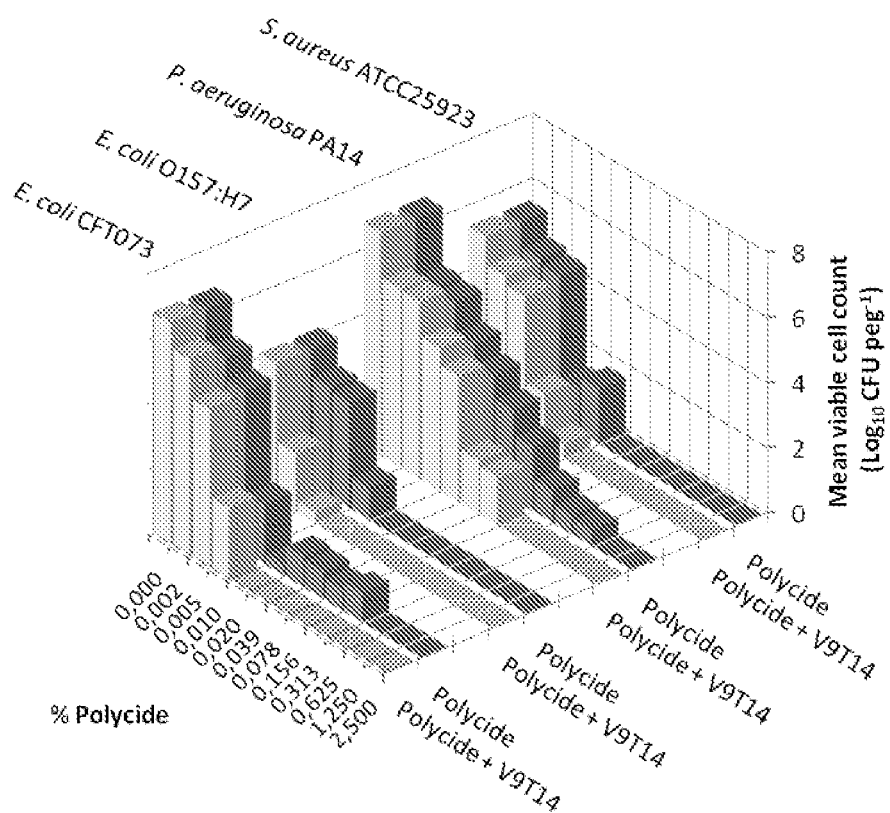
FIG. 35. Polycide susceptibility of different microorganisms after 30 min exposure. Biofilms were grown 24 h on the pegs of the CBD and then exposed to Polycide and Polycide associated to V9T14 biosurfactant. V9T14 biosurfactant was added to a final concentration of 5 µg/mL.

The association of V9T14 and Polycide allows a reduction of Polycide from 0.020% to 0.010% to obtain biofilm eradication (FIG. 35). The maximum increase in efficacy of about 2.9 $\log_{10}$ was observed at 0.005% of biocide.

*S. aureus* 25923

The killing efficacy of Polycide was increased of 1.2 $\log_{10}$ when V9T14 was present at 0.020% of biocide (FIG. 35).

Figure 36:
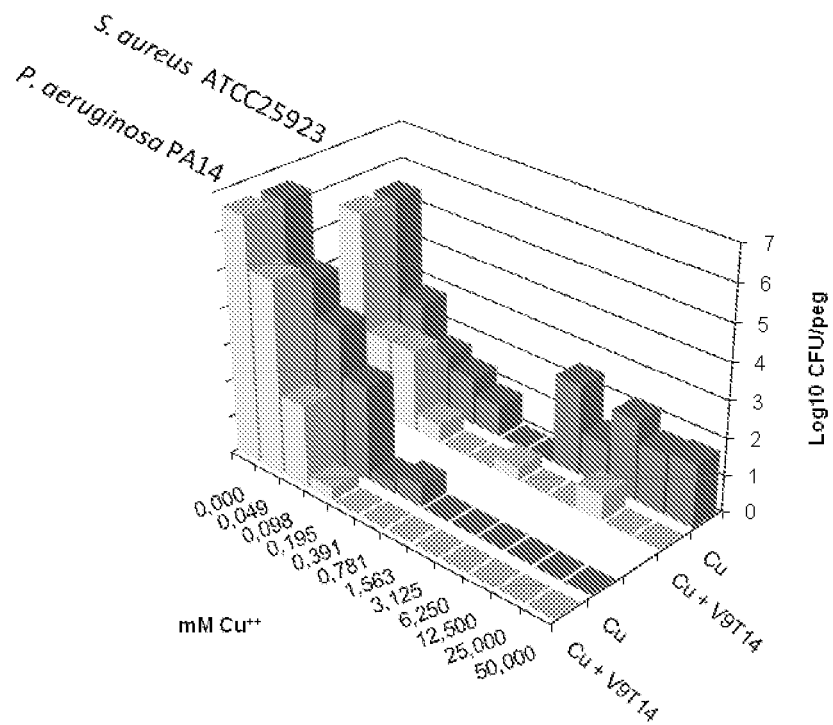
FIG. 36. Copper susceptibility of *P. aeruginosa* PA14 and *S. aureus* ATCC25923 after 8 h exposure. Biofilms were grown 24 h on the pegs of the CBD and then exposed to copper and copper associated with V9T14 biosurfactant. V9T14 biosurfactant was added to a final concentration of 5 µg/mL.

The concentration of copper to decrease biofilm viable cells below the threshold of detectable count was reduced by about 95% when V9T14 was present after 8 h exposure (FIG. 36). Maximum reduction of viable cell count was about 2.4 $\log_{10}$.

*P. aeruginosa* PA14

The concentration of Polycide to decrease biofilm viable cells below the threshold of detectable count was reduced from 1.250% to 0.156% when V9T14 was present (FIG. 35). The maximum reduction in viable cell count of about 1.1 $\log_{10}$ was observed at 0.039% of biocide.

The association with metals (silver or copper) was effective as well.

Figure 37:
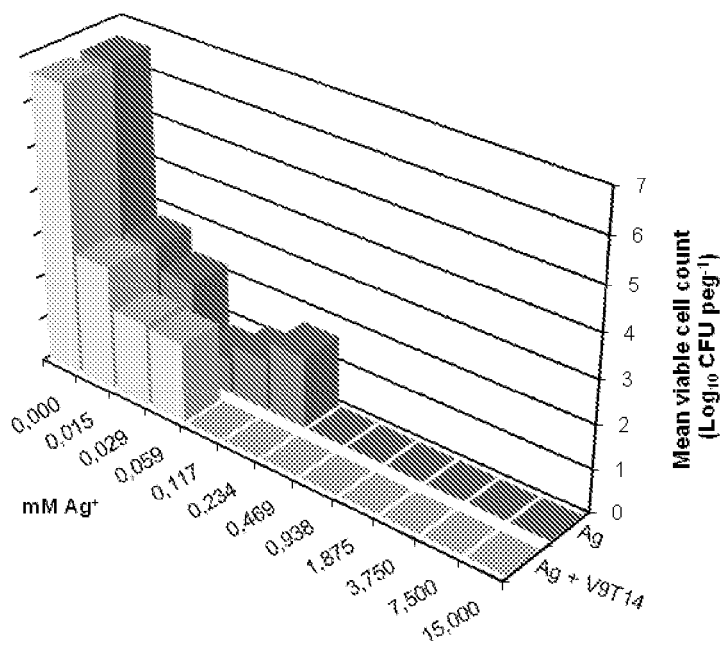
FIG. 37. Silver susceptibility of *P. aeruginosa* PA14 after 8 h exposure. Biofilms were grown 24 h on the pegs of the CBD and then exposed to silver and silver associated with V9T14 biosurfactant. V9T14 biosurfactant was added to a final concentration of 5 µg/mL.

Also the concentration of silver required to eradicate the biofilm was decreased from 0.469 mM to 0.117 mM when V9T14 was present (FIG. 37).

The concentration of $Cu^{2+}$ needed to eradicate the biofilm after 8 h of exposure was decreased from 1.563 mM to 0.391 mM when the metal was associated with V9T14, with a maximum increase of killing at 0.195 mM of about 2.2 $\log_{10}$ (FIG. 36).

References

Harrison, J. J., Ceri, H., Stremick, C., Turner, R. J., 2004. *Biofilm susceptibility to metal toxicity. Environ. Microbiol.* 6(12), 1220-1227.

Harrison J J, Ceri H, Yerly J, Stemick C A, Hu Y, Martinuzzi R, Turner R J, 2006. The use of microscopy and three-dimensional visualization to evaluate the structure of microbial biofilms cultivated in the Calgary Biofilm Device. Biol. Proced. Online 8(1): 194-215.

Harrison, J. J., Turner, R. J., Joo, D. A., Stan, M. A., Chan, C. S., Allan, N. D., Vrionis, H. A., Olson, M. E., Ceri, H. 2008. *Copper and quaternary ammonium cations exert synergistic bactericidal and antibiofilm activity against Pseudomonas aeruginosa.* Antimicrob. Agents. Chemother. 52(8), 2870-2881.

Morikawa, M., Hirata, Y., Imanaka, T., 2000. *A study on the structure-function of lipopeptide biosurfactants.* BBA—Mol. Cell. Biol. L. 1488. 211-218.

Teitzel, G. M., Parsek, M. R. 2003. *Heavy metal resistance of biofilm and planktonic Pseudomonas aeruginosa.* Appl. Environ. Microbiol. 69 (4): 2313-2320.

Waldeck, J., Meyer-Rammes, H., Wieland, S., Feesche, J., Maurer, K. H., 2007. *Targeted deletion of genes encoding extracellular enzymes in Bacillus licheniformis and the impact on the secretion capability.* J. Biotechnol. 130, 124-132.

Wang, J., Liu, J., Wang, X., Yao, J., Yu, Z., 2004. *Application of electrospray ionization mass spectrometry in rapid typing of fengycin homologues produced by Bacillus subtilis.* Letters Appl. Microbiol. 39, 98-102.

The invention claimed is:

1. A biosurfactant composition comprising a biosurfactant produced by a *Bacillus licheniformis* V9T14 strain deposited with Deutsche Sammlung von Mikroorganismen and Zellkulturen (DSMZ) with accession number DMS 21038, wherein the biosurfactant comprises surfactin and fengycin, wherein said composition comprises at least three surfactin molecules with fatty acid chains having lengths of 13, 14 and 15 carbon atoms.

2. The biosurfactant composition according to claim 1, wherein the three surfactin molecules are present with a relative ratio with respect to the fatty acid chain lengths $C_{13}$:$C_{14}$:$C_{15}$ comprised in the range 15-29%:9-23%:54-69%.

3. The biosurfactant composition according to claim 1, wherein said composition comprises at least fengycin A and fengycin B molecules having fatty acid chains with length of 14 to 18 carbon atoms.

4. The biosurfactant composition according to claim 3, wherein the fengycin A molecule has a fatty acid chain with length of 17 carbon atoms and is present in an amount comprised in the range 15-35% by weight, on the total weight of the composition fengycin molecules.

5. The biosurfactant composition according to claim 3, wherein the fengycin B molecule has a fatty acid chain with length of 17 carbon atoms, and is present in an amount comprised in the range 45-65% by weight, on the total weight of the composition fengycin molecules.

6. The biosurfactant composition according to claim 1, wherein said surfactin molecules are present in an amount comprised in the range 70-84% by weight, and said fengycin molecules are present in an amount comprised in the range 16-30% by weight, with respect to the total weight of the composition.

7. The biosurfactant composition according to claim 1 is for the treatment of an infection caused by bacteria able to grow planktonically and/or as a biofilm.

8. The biosurfactant composition according to claim 7, wherein the biosurfactant composition is in association with at least one biocide.

9. The biosurfactant composition according to claim 8, wherein the at least one biocide is selected among antibiotics, antibacterial agents, germicides and inorganic compounds able to kill bacteria.

10. The biosurfactant composition according to claim 9, wherein the antibiotic is selected among ampicillin, cefazolin, ceftriaxone, ciprofloxacin, tobramycin and trimethoprim/sulfmethoxazol.

11. The biosurfactant composition according to claim 7, wherein the biosurfactant composition, optionally in association with at least one biocide, is suitable for topical administration to a patient.

12. The biosurfactant composition according to claim 11, wherein the biosurfactant-composition, optionally in association with at least one biocide, is suitable for skin and/or mucosa applications.

13. The biosurfactant composition according to claim 7, wherein the biosurfactant composition, optionally in association with at least one biocide, is in the form of gel, cream, ointment, lotion, spray, salve, ophthalmic drop, ear drop, irrigation fluid, shampoo.

14. The biosurfactant composition according to claim 7, wherein the biosurfactant composition, optionally in association with at least one biocide, is applied to bandages, plasters.

15. A product containing the biosurfactant composition according to claim 1 and at least one biocide as a combined preparation for simultaneous, separate or sequential use for the treatment of an infection caused by bacteria able to grow planktonically and/or as a biofilm.

16. The product according to claim 15, wherein the bacterial biofilm is present on a biotic surface.

17. The product according to claim 15, wherein the at least one biocide is selected among antibiotics, antibacterial agents, germicides and inorganic compounds able to kill bacteria.

18. The product according to claim 17, wherein the antibiotic is selected among ampicillin, cefazolin, ceftriaxone, ciprofloxacin, tobramycin and trimethoprim/sulfmethoxazol.

19. The product according to claim 15, wherein the biosurfactant composition is used at a concentration comprised in the range 1 to 50 µg/mL.

20. The product according to claim 15, wherein the at least one biocide is used at a concentration comprised in the range 1 to 40 µg/mL.

21. The biosurfactant composition according to claim 1, wherein the three surfactin molecules are present with a relative ratio with respect to the fatty acid chain lengths $C_{13}:C_{14}:C_{15}$ comprised in the range 22%:16%:62%.

22. The biosurfactant composition according to claim 3, wherein the fengycin A molecule has a fatty acid chain with length of 17 carbon atoms and is present in an amount of 25% by weight, on the total weight of the composition fengycin molecules.

23. The biosurfactant composition according to claim 3, wherein the fengycin B molecule has a fatty acid chain with a length of 17 carbon atoms, and is present in an amount of 55% by weight, based on the total weight of the composition fengycin molecules.

24. The biosurfactant composition according to claim 1, wherein said surfactin molecules are present in an amount of 77% by weight, and said fengycin molecules are present in an amount of 23% by weight, with respect to the total weight of the biosurfactant composition.

25. The product according to claim 15, wherein the biosurfactant composition is used at a concentration comprised in the range 1 to 20 µg/mL.

26. The product according to claim 15, wherein the at least one biocide is used at a concentration comprised in the range 1 to 8 µg/mL.

* * * * *